United States Patent
KuKanich et al.

(10) Patent No.: US 11,771,662 B2
(45) Date of Patent: Oct. 3, 2023

(54) ANALGESIC FORMULATION FOR CONTROL OF PAIN IN DOGS

(71) Applicants: Kansas State University Research Foundation, Manhattan, KS (US); Charles W. Locuson, Wenham, MA (US)

(72) Inventors: Stanley KuKanich, Manhattan, KS (US); Katherine KuKanich, Manhattan, KS (US); Charles W. Locuson, Wenham, MA (US); David Rankin, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 96 days.

(21) Appl. No.: 16/644,776

(22) PCT Filed: Sep. 5, 2018

(86) PCT No.: PCT/US2018/049589
§ 371 (c)(1),
(2) Date: Mar. 5, 2020

(87) PCT Pub. No.: WO2019/050974
PCT Pub. Date: Mar. 14, 2019

(65) Prior Publication Data
US 2021/0077426 A1  Mar. 18, 2021

Related U.S. Application Data

(60) Provisional application No. 62/554,385, filed on Sep. 5, 2017.

(51) Int. Cl.
*A61K 31/137* (2006.01)
*A61P 23/00* (2006.01)
(Continued)

(52) U.S. Cl.
CPC .......... *A61K 31/137* (2013.01); *A61K 9/0019* (2013.01); *A61K 9/0053* (2013.01);
(Continued)

(58) Field of Classification Search
CPC .............. A61K 31/137; A61K 31/4196; A61K 31/485; A61P 23/00
See application file for complete search history.

(56) References Cited

U.S. PATENT DOCUMENTS

2007/0110805 A1    5/2007  Levinson et al.
2012/0231092 A1*   9/2012  Oronsky .............. A61K 31/485
                                                            424/722
(Continued)

OTHER PUBLICATIONS

KuKanich et al.; "The effects of concurrent administration of cytochrome P-450 inhibitors on the pharmacokinetics of oral methadone in healthy dogs"; 2011; Veterinary Anaesthesia and Analgesia; 38:224-230; doi:10.1111/j.1467-2995.2011.00602.x (Year: 2011).*

(Continued)

*Primary Examiner* — Timothy P Thomas
(74) *Attorney, Agent, or Firm* — Hovey Williams LLP

(57) ABSTRACT

Provided herein are treatments for reducing pain in dogs. The treatments generally comprise a combination of an opioid compound, such as methadone, and an azole compound, such as fluconazole. The treatments may further comprise an opioid abuse deterrent that advantageously inhibits opioid effects in humans while maintaining desirable analgesic effects in dogs. Additionally, the treatments provided herein avoid the undesirable side effects of prior art opioid treatments for dogs. The treatments may be administered as separate doses or in a single formulation product for improved compliance. The treatments have wide use potential in dogs from perioperative patients to inpatients and outpatients and may be used, for example, for sedation (Continued)

in minor procedures, analgesia, and decreasing temperature in canine patients.

28 Claims, 15 Drawing Sheets

(51) Int. Cl.
```
A61K 31/4196   (2006.01)
A61K 31/485    (2006.01)
A61K 9/00      (2006.01)
A61K 9/08      (2006.01)
A61K 31/427    (2006.01)
A61K 31/44     (2006.01)
A61K 31/451    (2006.01)
A61K 31/454    (2006.01)
A61K 31/496    (2006.01)
A61K 31/506    (2006.01)
A61K 31/517    (2006.01)
A61K 47/10     (2017.01)
A61K 47/34     (2017.01)
```
(52) U.S. Cl.
CPC ............ *A61K 9/08* (2013.01); *A61K 31/4196* (2013.01); *A61K 31/427* (2013.01); *A61K 31/44* (2013.01); *A61K 31/451* (2013.01); *A61K 31/454* (2013.01); *A61K 31/485* (2013.01); *A61K 31/496* (2013.01); *A61K 31/506* (2013.01); *A61K 31/517* (2013.01); *A61K 47/10* (2013.01); *A61K 47/34* (2013.01); *A61P 23/00* (2018.01)

(56) References Cited

U.S. PATENT DOCUMENTS

2013/0295088 A1    11/2013  Poulsen et al.
2019/0247300 A1*   8/2019   Ray, II .................. A61K 45/06

OTHER PUBLICATIONS

Walter et al.; "Abuse-Deterrent Opioid Formulations: Pharmacokinetic and Pharmacodynamic Considerations"; 2016 (published 2015); Clin. Pharmacokinet.; 55:751-767; DOI:10.1007/s40262-015-0362-3 (Year: 2015).*

Cobb et al.; "The effect of fluconazole on the clinical pharmacokinetics of methadone"; 1998; Clin. Pharmacol. Ther.; 63:655-62 (Year: 1998).*

Reagan-Shaw et al.; "Dose Translation from animal to human studies revisited"; 2007; The FASEB Journal; 22: 659-661 (Year: 2007).*

Chou; "Theoretical Basis, Experimental Design, and Computerized Simulation of Synergism and Antagonism in Drug Combination Studies"; 2006; Pharacological Reviews; 58(3): 621-681 (Year: 2006).*

International Search Report and Written Opinion in corresponding PCT/US2018/049589, dated Nov. 20, 2018.

Kukanich, et al., "Clinical pharmacology of nonsteroidal antiinflammatory drugs in dogs", Vet Anaesth Analg., Jan. 2012;39(1):69-90.

Kyles, et al., "Disposition of transdermally administered fentanyl in dogs", Am J Vet Res., May 1996;57(5):715-9.

Egger, et al., "Comparison of plasma fentanyl concentrations by using three transdermal fentanyl patch sizes in dogs", Vet Surg., Mar.-Apr. 1998;27(2):159-66.

Pettifer, et al., "The effect of inhalant anesthetic and body temperature on peri-anesthetic serum concentrations of transdermally administered fentanyl in dogs", Vet Anaesth Analg., Apr. 2004;31(2):109-20.

Schmiedt, et al., "Accidental prehension and suspected transmucosal or oral absorption of fentanyl from a transdermal patch in a dog", Vet Anaesth Analg., Jan. 2007;34(1):70-3.

Kukanich, "Outpatient oral analgesics in dogs and cats beyond nonsteroidal antiinflammatory drugs: an evidence-based approach", Vet Clin North Am Small Anim Pract., Sep. 2013;43(5):1109-25.

Weinstein, et al., "Determination of oxycodone in plasma and identification of a major metabolite", J Pharm Sci., Apr. 1979;68(4):527-8.

Aungst, et al., "Oral and rectal nalbuphine bioavailability: first-pass metabolism in rats and dogs", Biopharm Drug Dispos., Oct.-Dec. 1985;6(4):413-21.

Ritschel, et al., "Meperidine pharmacokinetics following intravenous, peroral and buccal administration in beagle dogs", Methods Find Exp Clin Pharmacol., Dec. 1987;9(12):811-5.

Kukanich, et al., "The effects of inhibiting cytochrome P450 3A, p-glycoprotein, and gastric acid secretion on the oral bioavailability of methadone in dogs", J Vet Pharmacol Ther., Oct. 2005;28(5):461-6 (abstract attached).

Kukanich, et al., "Pharmacokinetics of hydrocodone and hydromorphone after oral hydrocodone in healthy Greyhound dogs", Vet J., May 2013;196(2):266-8.

Benitez, et al., "Pharmacokinetics of hydrocodone and tramadol administered for control of postoperative pain in dogs following tibial plateau leveling osteotomy", Am J Vet Res., Sep. 2015;76(9):763-70.

Kukanich, et al., "The effects of concurrent administration of cytochrome P-450 inhibitors on the pharmacokinetics of oral methadone in healthy dogs". Vet Anaesth Analg., May 2011;38(3):224-30.

Kukanich, et al., "Pharmacokinetics and pharmacodynamics of oral acetaminophen in combination with codeine in healthy Greyhound dogs", J Vet Pharmacol Ther., Oct. 2016;39(5):514-7.

Kukanich, et al., "Chloramphenicol significantly affects the pharmacokinetics of oral methadone in Greyhound dogs", Vet Anaesth Analg., Nov. 2015;42(6):597-607.

Kukanich, et al., "The disposition and behavioral effects of methadone in Greyhounds", Vet Anaesth Analg., May 2008;35(3):242-8.

Abbo, et al., "Pharmacokinetics of buprenorphine following intravenous and oral transmucosal administration in dogs", Vet Ther., 2008 Summer;9(2):83-93.

Ko, et al., "Efficacy of oral transmucosal and intravenous administration of buprenorphine before surgery for postoperative analgesia in dogs undergoing ovariohysterectomy", J Am Vet Med Assoc., Feb. 1, 2011;238(3):318-28.

Moryl, et al., "A phase I study of D-methadone in patients with chronic pain", J Opioid Manag., Jan.-Feb. 2016;12(1):47-55.

Kristensen, et al., "The mu1, mu2, delta, kappa opioid receptor binding profiles of methadone stereoisomers and morphine", Life Sci., 1995;56(2):PL45-50.

Haumann, et al., "Methadone is superior to fentanyl in treating neuropathic pain in patients with head-and-neck cancer", Eur J Cancer., Sep. 2016;65:121-9.

Yunis, "Chloramphenicol: relation of structure to activity and toxicity", Annu Rev Pharmacol Toxicol., 1988;28:83-100.

Perez, et al., "Tramadol metabolism to O-desmethyl tramadol (M1) and N-desmethyl tramadol (M2) by dog liver microsomes: Species comparison and identification of responsible canine cytochrome P-450s (CYPs)", Program in Individualized Medicine, Oct. 6, 2016 (43 pages).

Aidasani, et al., "In vitro drug-drug interaction screens for canine veterinary medicines: evaluation of cytochrome P450 reversible inhibition", Drug Metab Dispos., Aug. 2008;36(8):1512-8.

Katayama, et al., "Fluconazole decreases cyclosporine dosage in renal transplanted dogs", Res Vet Sci., Aug. 2010;89(1):124-5.

Katayama, et al., "Effect of multiple oral dosing of fluconazole on the pharmacokinetics of cyclosporine in healthy beagles", J Vet Med Sci., Jan. 2008;70(1):85-8.

Mazepa, et al., "Retrospective comparison of the efficacy of fluconazole or itraconazole for the treatment of systemic blastomycosis in dogs", J Vet Intern Med., May-Jun. 2011;25(3):440-5.

Court, "Canine cytochrome P-450 pharmacogenetics", Vet Clin North Am Small Anim Pract., Sep. 2013;43(5):1027-38.

(56) References Cited

OTHER PUBLICATIONS

Kase, et al., "A New Potent Non-narcotic Antitussive, 1-Methyl-3-di (2-thienyl) methylenepiperidine", Chem Pharm Bull (Tokyo), 1959;7:372-377.
Anonymous, "Committee for veterinary medicinal products: levomethadone summary report", European Agency for the Evaluation of Medicinal Products, EMEA/MRT/585/99-Final, 1999.
Kukanich, "Analgesia and pain assessment in veterinary research and clinical trials", Vet J., Apr. 2011; 188(1):1-2.
Guedes, et al., "Pharmacokinetics and physiological effects of intravenous hydromorphone in conscious dogs", J Vet Pharmacol Ther., Aug. 2008;31(4):334-43.

* cited by examiner

ANALGESIC FORMULATION FOR CONTROL OF PAIN IN DOGS

CROSS-REFERENCE TO RELATED APPLICATIONS

The present application is the U.S. National Stage of International Patent Application No. PCT/US2018/049589, filed Sep. 5, 2018, which claims the priority benefit to U.S. Provisional Patent Application No. 62/554,385 filed on Sep. 5, 2017, entitled ANALGESIC FORMULATION FOR CONTROL OF PAIN IN DOGS, each of which is incorporated by reference in its entirety herein.

BACKGROUND OF THE INVENTION

Field of the Invention

The present invention is generally directed to analgesic treatments for dogs comprising an opioid compound in combination with an azole compound.

Description of the Prior Art

The options for treating moderate to severe pain in dogs is very limited. Nonsteroidal anti-inflammatory drugs have efficacy limited to mild to moderate pain and can have adverse effects ranging from mild to severe including gastrointestinal ulcerations and perforations, renal failure and death. Injectable opioids are frequently used for inpatients, but they are short acting (2-6 hours duration) and are not practical for outpatients. Long-acting (12-hour duration) and effective injectable opioids are desirable for in-hospital use, but oral opioids would be preferred for outpatient use. Sending home injectable opioids with clients presents a risk for inadvertent drug exposure, misuse, and diversion. The most desirable outpatient therapy would be an oral long acting opioid with an abuse/misuse deterrent that also acts as a safety mechanism if inadvertent human exposure occurs. A Food and Drug Administration (FDA) approved fentanyl transdermal solution for use in dogs was recently discontinued by the manufacturer and is no longer available. Fentanyl transdermal patches have been studied in dogs but are variably absorbed; absorption is affected by body temperature and the patches present an ingestion and exposure hazard for dogs and humans due to the high drug content. Other options including gabapentin, pregabalin, tricyclic antidepressants and nutraceuticals are not proven to provide analgesia in dogs.

Oral opioids have been described as having low and inconsistent bioavailability in dogs. Oral transmucosal absorption of buprenorphine in dogs has been demonstrated, but produces low, inconsistent and a brief duration of buprenorphine exposure. An option to enhance the oral drug bioavailability and prolong the duration of drug exposure is to co-administer a drug that decreases the metabolism of the analgesic drug. Initial studies administering a higher dose of oral methadone (2 mg/kg PO) with drugs to decrease metabolism resulted in higher than expected methadone plasma concentrations and prominent opioid effects including hypothermia and bradycardia in addition to sedation and panting in comparison to oral methadone alone. Oral methadone at a lower dose (1 mg/kg) with the metabolism inhibitor chloramphenicol resulted in significantly higher methadone plasma concentrations and prolonged duration of plasma concentrations compared to methadone alone and was well tolerated. The combination of methadone and chloramphenicol increased the relative oral bioavailability of methadone by 900% and the elimination half-life from 1.1 to 5.8 hours compared to oral methadone alone. Methadone administered with chloramphenicol also produced clinical signs associated with opioids (panting and sedation) after administration, but not after oral methadone alone.

Chloramphenicol produced desirable effects on oral methadone pharmacokinetics in dogs including increased bioavailability and prolonged duration of methadone plasma concentrations, but potential adverse effects of chloramphenicol precludes its widespread use. Since chloramphenicol is an antibiotic it may select for bacterial resistance. Chloramphenicol is also associated with irreversible aplastic anemia in humans treated with systemic chloramphenicol and the risk to humans with casual exposure has not been well defined. Therefore, what is needed is a treatment that decreases methadone metabolism with minimal side effects.

SUMMARY OF THE INVENTION

In one embodiment, there is provided a method of providing an analgesic effect in a dog. The method comprises administering to the dog an opioid compound and an azole compound. In certain embodiments, the method further comprises administering to the dog an abuse deterrent, such as an opioid antagonist, that may provide a human misuse/abuse deterrent and safety mechanism but will not adversely affect the pain reducing and analgesic effects in the dog.

In another embodiment, there is provided an analgesic pharmaceutical composition for reducing pain in a dog. The composition comprises an opioid compound and an azole compound. In certain embodiments, the composition further comprises an abuse deterrent, such as an opioid antagonist.

In another embodiment, there is provided an analgesic pharmaceutical composition for reducing pain in a dog. The composition comprises methadone or a methadone enantiomer, fluconazole, and naltrexone.

In another embodiment, there is provided a liquid analgesic pharmaceutical composition for reducing pain in a dog. The liquid composition comprises methadone or a methadone enantiomer, and from about 10 mg/mL to about 50 mg/mL of fluconazole.

BRIEF DESCRIPTION OF THE DRAWINGS

Figure (FIG. 1 is a chart showing change in rectal temperature after administration of methadone alone (1 mg/kg), methadone (1 mg/kg) 24 hr after initiating fluconazole 5 mg/kg PO q 12 h, methadone (1 mg/kg) 24 hr after initiating fluconazole 2.5 mg/kg PO q 12 h, and methadone (1 mg/kg) 24 hr after initiating fluconazole 5 mg/kg PO q 24.

DETAILED DESCRIPTION OF THE PREFERRED EMBODIMENT

Figure 1:
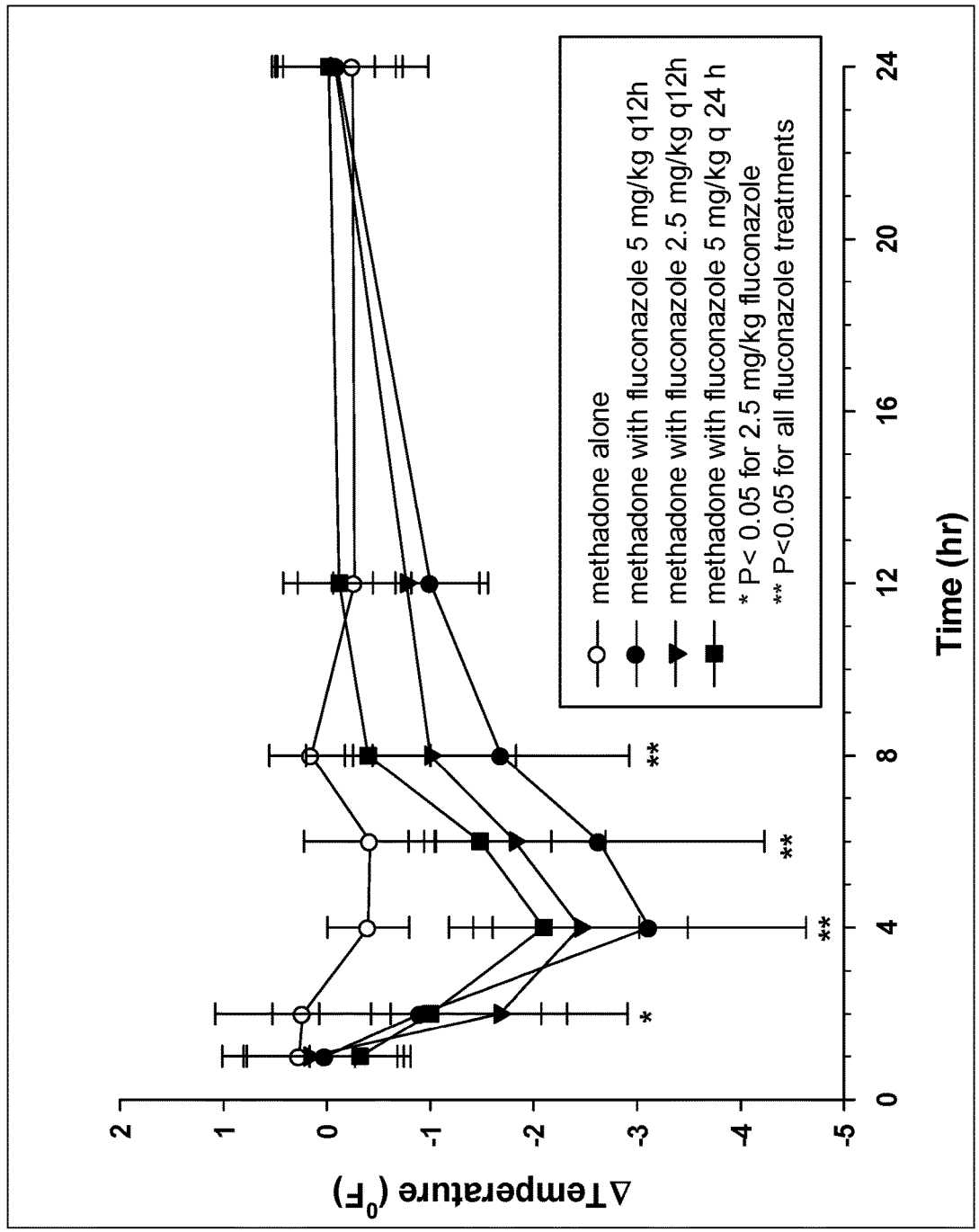

Embodiments of the present invention are generally directed to treatments for reducing the pain in dogs using the combination of an opioid compound and an azole compound. The treatments advantageously impart the desirable antinociceptive effects upon dogs, without the undesirable side effects typical of prior art opioid treatments. The treatments can also be combined with an abuse deterrent (e.g., opioid antagonist) while still maintaining sufficient antinociceptive effects.

Methods in accordance embodiments of the present invention provide an analgesic effect in a dog. The methods generally comprise administering to the dog an opioid compound and an azole compound. The opioid compound may be any of a number of known natural (e.g., opiate) or synthetic compounds that act on opioid receptors to impart an analgesic effect in the dog. In certain embodiments, the opioid compound is selected from the group consisting of methadone, methadone enantiomers, codeine, morphine, hydrocodone, oxycodone, meperidine, nalbuphine, buprenorphine, butorphanol, fentanyl and combinations thereof. In certain preferred embodiments, the opioid compound is methadone. Methadone is a racemic mixture of levomethadone which primarily produces mu opioid agonist effects and dextromethadone which produces weak mu opioid effects, but prominent N-methyl D-aspartate (NMDA) antagonist effects. Therefore, both methadone enantiomers can contribute to analgesia. In certain embodiments, racemic methadone may be used, for example, to produce better clinical effects than pure mu opioid agonists for neuropathic and cancer pain. Methadone is approved as an injectable analgesic for dogs in some countries. In the United States, methadone is an FDA approved drug for human use as an injectable solution and various oral formulations including oral tablets and oral solution. Extralabel use of methadone is allowed in the United States according to the Animal Medicinal Drug Use Clarification Act (AMDUCA).

The azole compound can be any of a number of known compounds comprising the five-membered heterocyclic azole or derivatives thereof. In certain embodiments, the azole antifungal compound is a triazole antifungal (antimycotic) compound. In certain such embodiments, the azole compound is a triazole antifungal compound selected from the group consisting of albaconazole, efinaconazole, epoxiconazole, fluconazole, isavuconazole, itraconazole, posaconazole, propiconazole, ravuconazole, terconazole, voriconazole, and combinations thereof. In certain preferred embodiments, the azole compound is fluconazole. Fluconazole is a triazole compound typically used as an antifungal medication. However, when used in combination with an opioid compound in accordance with embodiments of the present invention, fluconazole is effective at prolonging the duration of desirable opioid analgesic effects while reducing the occurrence of less desirable side effects. Fluconazole is well tolerated in dogs, even with chronic therapy, and there are no known irreversible human health concerns from casual exposure to fluconazole.

A minor drug interaction has been shown in humans equivalent to about a 1.30 to 1.35 fold (30-35%) increase in methadone drug exposure when fluconazole is administered with methadone. Fluconazole is considered a weak inhibitor of methadone metabolism in humans resulting in ≥1.25 to <2-fold increase in the methadone area under the curve (AUC). Embodiments of the present invention, however, demonstrated a strong interaction (>5 fold) increase in the AUC with at least a 64-fold (6400%) increase in the AUC of methadone when administered with fluconazole in dogs.

The opioid compound and azole compound can be administered in a variety of dosing schemes. In certain embodiments, the opioid compound and azole compound are administered to the dog at a dose weight (mg/kg) ratio of opioid compound to azole compound of about 1:1 to about 1:20, preferably about 1:2 to about 1:10, and more preferably about 1:2.5 to about 1:5. The size of the dose of each component may depend on a variety of factors. However, in certain embodiments, the opioid compound is administered at a dose of about 0.01 mg/kg to about 10 mg/kg, preferably about 0.1 mg/kg to about 5 mg/kg, and more preferably about 0.5 mg/kg to about 2 mg/kg. In certain embodiments, the azole compound is administered at a dose of about 0.02 mg/kg to about 20 mg/kg, preferably about 0.2 mg/kg to about 10 mg/kg, and more preferably about 1 mg/kg to about 5 mg/kg. In certain embodiments, the opioid compound and azole compound are administered as a single dose providing prolonged analgesic effect. In certain embodiments, the administering comprises a first dose of the opioid compound and the azole compound concurrently, and a second dose of the opioid compound and the azole compound about 4 hours to about 24 hours, preferably about 6 hours to about 18 hours, and more preferably about 10 hours to about 14 hours after the first dose. Third, fourth, etc. doses can also be administered in the same manner. In certain other embodiments, the administering comprises administering a dose of the azole compound from concurrently/simultaneously to about 48 hours, preferably about 24 hours, and more preferably to about 14 hours before a separate dose of the opioid compound.

The opioid compound and the azole compound can be administered by a variety of delivery methods and pharmaceutical carriers. Additionally, the opioid compound and the azole compound can be administered in the same or different delivery methods and pharmaceutical carriers. In certain embodiments, the opioid compound and/or the azole compound is administered by enteral administration, and more preferably oral administration (i.e., per os). In certain other embodiments, the opioid compound and/or the azole compound is administered as a parenteral formulation. The opioid compound and azole compound can be administered as separate compositions or combined in a single pharmaceutical composition. In certain preferred embodiments, the opioid compound and azole compound are administered as a single pharmaceutical composition. For example, in certain embodiments, the opioid compound and azole compound are combined in a single pharmaceutical composition in a form selected from the group consisting of tablet, capsule, solution, or suspension. In certain such embodiments, and particularly when used as a parenteral formulation, the opioid compound and azole compound are combined in a single pharmaceutical composition in the form of a liquid suspension or solution comprising polyethylene glycol, ethanol, and/or water. In such certain embodiments, the liquid pharmaceutical composition comprises from about 20% to about 80% by weight, preferably about 30% to about 60% by weight, and more preferably about 40% to about 50% by weight of polyethylene glycol. Although fluconazole is generally poorly soluble in water, in certain embodiments, the fluconazole can be present in the liquid suspension or solution at a concentration up to at least 50 mg/mL. In certain embodiments, the pharmaceutical composition is a liquid composition comprising about 10 mg/mL to about 50 mg/mL, preferably about 15 mg/mL to about 40 mg/mL, and more preferably about 20 mg/mL to about 30 mg/mL of fluconazole. However, in certain embodiments, the liquid composition can comprise greater than about 50 mg/mL of fluconazole.

In certain embodiments, the pharmaceutical composition further comprises an abuse deterrent. As used herein, an "abuse deterrent" refers to a component having properties to deter human abuse of the opioid compound. In certain embodiments, the abuse deterrent can also provide a safety feature if the formulation is accidently ingested (e.g. a child ingesting the formulation). In certain embodiments, the abuse deterrent is an opioid antagonist, and specifically an opioid antagonist in humans but not in dogs when administered as described. In certain embodiments, the abuse deterrent is an opioid antagonist selected from the group consisting of naltrexone, naloxone, nalmefene and pharmaceutically acceptable salts thereof. In certain preferred embodiments, the abuse deterrent is naltrexone. Naltrexone is an opioid antagonist that will antagonize opioid effects and elicit signs of withdrawal in humans if ingested or injected, particularly when administered at a ratio of 6.25:1 to 25:1 (methadone:naltrexone). However, naltrexone has a low oral bioavailability and short half-life (rapid elimination) in dogs when combined with methadone and an azole compound such as fluconazole, and will not antagonize the opioid with by direct interaction or interactions of an active metabolite (e.g. β-naltrexol). Therefore, naltrexone can act as an abuse deterrent and safety mechanism for humans but will not antagonize opioid effects in dogs. In certain embodiments, the opioid compound and abuse deterrent (e.g., naltrexone) are administered to the dog at a dose weight (mg/kg) ratio of opioid compound to abuse deterrent of about 30:1 to about 1:1, preferably about 20:1 to about 2:1, and more preferably about 10:1 to about 3:1. In certain embodiments, the abuse deterrent is administered at a dose of about 0.001 mg/kg to about 5 mg/kg, preferably about 0.01 mg/kg to about 1 mg/kg, and more preferably about 0.1 mg/kg to about 0.5 mg/kg.

The pharmaceutical composition may also comprise additives such as flavorings, thickeners, binders, surfactants, and other texture modifiers. Such additives are particularly useful in compositions for oral administration. The pharmaceutical composition may also comprise pH buffers, adjuvants, or other additives that are particularly suitable for parenteral administration, including injections. However, in certain embodiments, the pharmaceutical composition consists of (or consists essentially of) the opioid compound and the azole compound. In certain other embodiments, the pharmaceutical composition consists of (or consists essentially of) the opioid compound, the azole compound, and the abuse deterrent. In certain embodiments, a liquid carrier (such as water or ethanol) or other additives described above may also be present in the composition without materially affecting the basic and novel characteristics of the present invention.

Advantages of treatments comprising an opioid compound (e.g., methadone) and azole compound (e.g., fluconazole) are numerous. A special formulation is unnecessary for controlled or sustained release, since a conventional tablet/capsule/liquid formulation containing both drugs is sufficient. A conventional oral formulation does not require sterile processing facilities, in contrast to extended release injectable formulations. A parenteral formulation enables administration with prolonged dosing intervals when oral administration is not feasible. The active pharmaceutical ingredients are readily available, non-proprietary, and safe in dogs. Due to the low oral bioavailability of opioid antagonists (e.g. naltrexone) in dogs, sequestration of naltrexone in the manufacturing of the formulation is not needed. As described herein, methadone combined with fluconazole is capable of showing clinical opioid effects for prolonged periods in dogs, which reduces the number of doses to be administered and allows for excellent dosing compliance and addition of naltrexone does not antagonize those desired effect.

Although the components can be administered separately, the convenience of administering a single pharmaceutical composition compared to two separate drugs results in compliance advantage. The cost of producing a single pharmaceutical composition is also likely less than producing separate formulations (economic advantage). The single product can also be produced as a flavored tablet/liquid formulation, resulting in administration convenience and compliance advantage. Finally, additional steps can be implemented by incorporating an anti-drug diversion/abuse deterrent resulting in a single pharmaceutical composition with three separate drugs.

Oral and parenteral opioid and azole compound treatments in accordance with embodiments of the present invention have wide use potential in dogs from perioperative patients to inpatients that suffered severe trauma to potentially even outpatients for animals intolerant of or with pain poorly controlled by nonsteroidal anti-inflammatory drugs (e.g. cancer pain, neuropathic pain, severe osteoarthritis). Uses include sedation for minor procedures, analgesia, decreasing temperature in febrile in-patient dogs in addition to other opioid effects not specifically assessed, but previously described including antitussive effects.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than or equal to about 10" (with no upper bounds) and a claim reciting "less than or equal to about 100" (with no lower bounds).

EXAMPLES

The following examples set forth efficacy studies of treatments comprising an opioid compound (methadone) in combination with an azole compound (fluconazole) and/or an abuse deterrent (naltrexone). It is to be understood, however, that these examples are provided by way of illustration and nothing therein should be taken as a limitation upon the overall scope of the invention.

Example I

Figure 2:
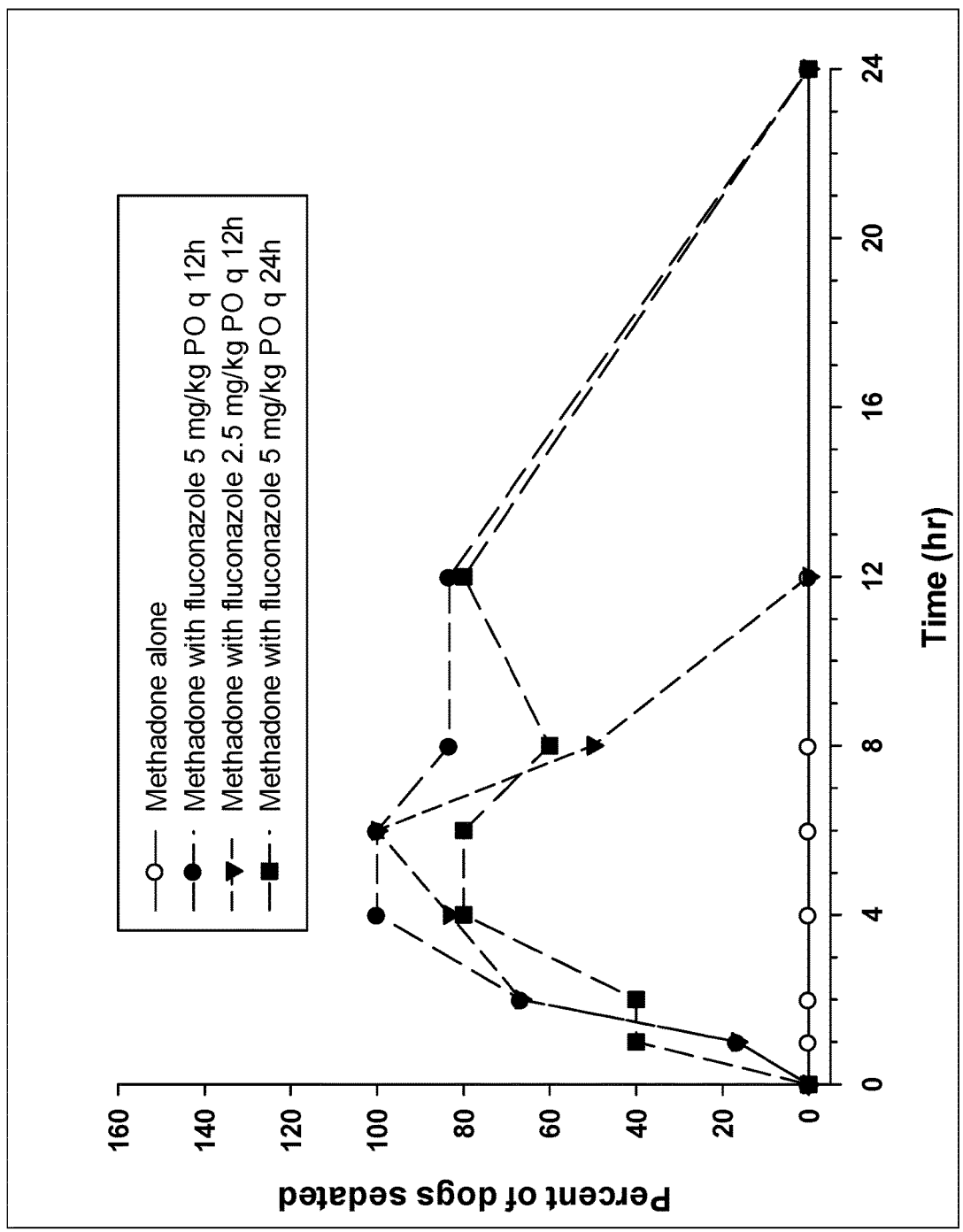
FIG. 2 is a chart showing sedation after administration of methadone alone (1 mg/kg), methadone (1 mg/kg) 24 hr after initiating fluconazole 5 mg/kg PO q 12 h, methadone (1 mg/kg) 24 hr after initiating fluconazole 2.5 mg/kg PO q 12 h, and methadone (1 mg/kg) 24 hr after initiating fluconazole 5 mg/kg PO q 24.

As described herein, preliminary studies in groups of 6 healthy dogs have identified significant opioid effects when oral methadone is administered with oral fluconazole, but not when oral methadone is administered alone. The treatment groups included methadone administered alone at a single dose of 1 mg/kg PO (mg of treatment per kg of body weight, per os—by mouth), methadone administered as a single dose (1 mg/kg PO) 24 hours after fluconazole (5 mg/kg PO q 12 hr), methadone administered as a single dose (1 mg/kg PO) 24 hours after fluconazole (2.5 mg/kg PO q 12 hr) and methadone administered as a single dose (1 mg/kg PO) 24 hours after fluconazole (5 mg/kg PO q 24 hr). Fluconazole administered 24 hours prior to methadone resulted in significant decreases in rectal temperature when administered at 2.5 mg/kg, 5 mg/kg orally every 12 hr or 5 mg/kg orally every 24 hr (FIG. 1) for at least 8 hours after administration. Body temperature was also decreased 12 hours after administration but was not significant in dogs administered fluconazole. Sedation (see Table 1) was not noted in any of the dogs at any time point with methadone alone but was observed in all groups administered fluconazole with methadone (FIG. 2) for 8-12 hours.

TABLE 1

Scoring rubric for sedation assessment.

| Sedation score | Description |
| --- | --- |
| None | No apparent effect |
| Mild | Drowsy, but still active |
| Moderate | Drowsy, decreased activity, glazed eyes, but still able to walk without assistance |
| Heavy | Very drowsy, unable to walk or requires assistance to walk |

Plasma concentrations of methadone were determined by a validated liquid chromatography triple quadrupole mass spectrometry method. In all 6 dogs administered methadone alone, plasma concentrations failed to exceed 2 ng/mL and the total drug exposure, measure by the area under the curve (AUC) extrapolated to infinity was low (Table 2).

TABLE 2

Plasma methadone concentrations (ng/mL) determined by liquid chromatography/triple quadrupole mass spectrometry and the area under the curve in 6 dogs administered methadone 1 mg/kg PO.

| Time (hr) | Dog 1 | Dog 2 | Dog 3 | Dog 4 | Dog 5 | Dog 6 | Mean | SD |
| --- | --- | --- | --- | --- | --- | --- | --- | --- |
| 0 | <0.5 | <0.5 | <0.5 | <0.5 | <0.5 | <0.5 | | |
| 0.333 | <0.5 | 1.3 | <0.5 | 1.9 | 1.3 | 0.8 | 0.9 | |
| 0.667 | 1.9 | 1.2 | 0.7 | 1.3 | 1.5 | 1.0 | 1.3 | 0.4 |
| 1 | 1.0 | 1.2 | 1.5 | 1.4 | 1.2 | 1.1 | 1.2 | 0.2 |
| 2 | <0.5 | 0.8 | 1.3 | <0.5 | 0.6 | 0.9 | 0.7 | 0.5 |
| 4 | <0.5 | <0.5 | 1.0 | 0.5 | <0.5 | 0.7 | 0.4 | 0.4 |
| 6 | <0.5 | <0.5 | <0.5 | <0.5 | <0.5 | <0.5 | | |
| 8 | <0.5 | <0.5 | <0.5 | <0.5 | <0.5 | <0.5 | | |
| 12 | <0.5 | <0.5 | <0.5 | <0.5 | <0.5 | <0.5 | | |
| 24 | <0.5 | <0.5 | <0.5 | <0.5 | <0.5 | <0.5 | | |
| Mean dose normalized AUC (to infinity) (hr*ng/mL) | | | | | | | 6.1 | |

Figure 3:
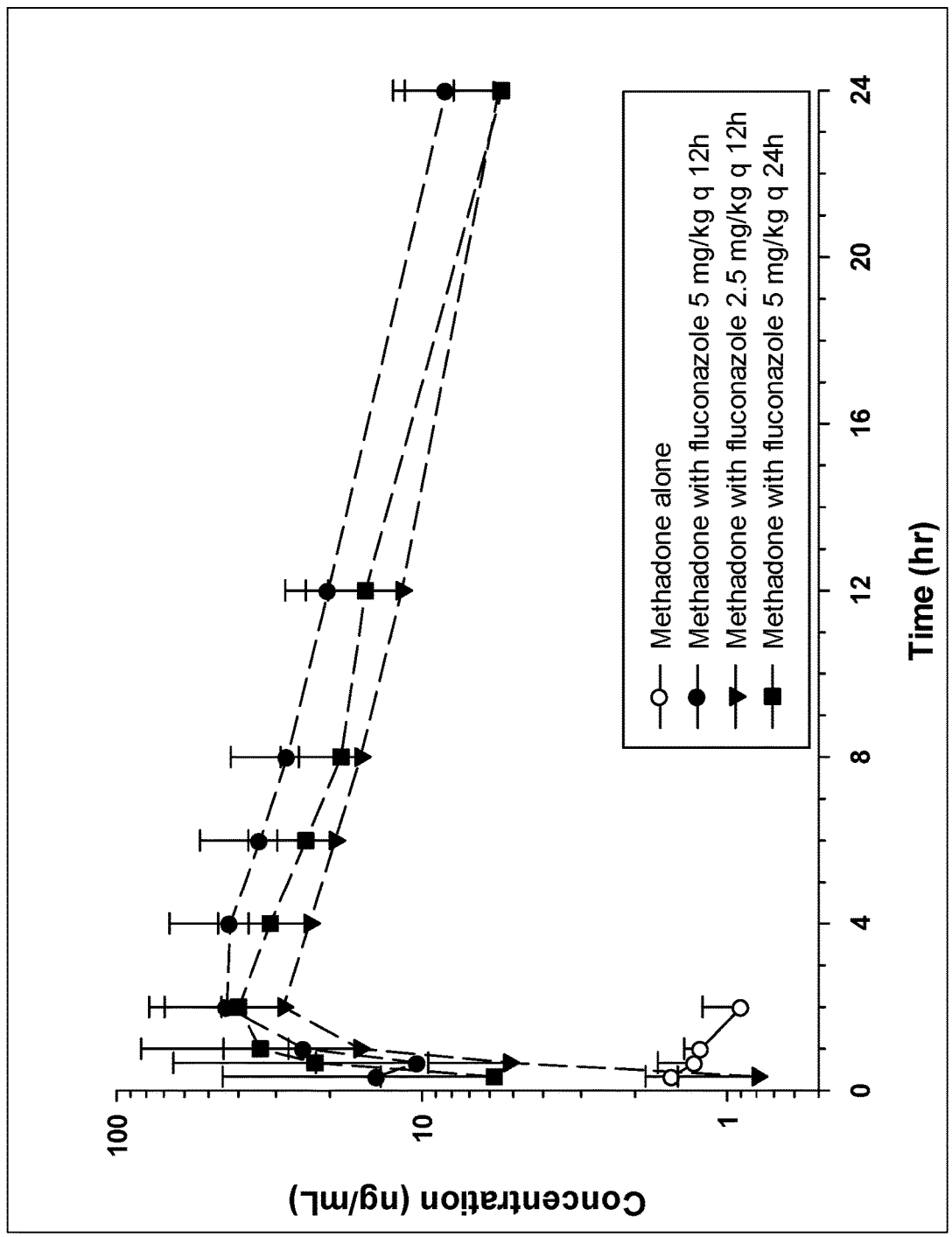
FIG. 3 is a chart showing plasma methadone concentrations (y-axis) versus time (x-axis) in four groups of six dogs each administered methadone alone (1 mg/kg), methadone (1 mg/kg) 24 hr after initiating fluconazole 5 mg/kg PO q 12 h, methadone (1 mg/kg) 24 hr after initiating fluconazole 2.5 mg/kg PO q 12 h, and methadone (1 mg/kg) 24 hr after initiating fluconazole 5 mg/kg PO q 24 h.

Mean methadone plasma concentrations exceeded 10 ng/mL in all groups administered methadone with fluconazole from at least 1 hour post administration through 12 hours post administration (Table 3, FIG. 3). The mean relative oral bioavailabilities (area under the curve extrapolated to infinity of the fluconazole treatment groups divided by the area under the curve extrapolated to infinity of the methadone alone group) were 6459-11946% indicating substantial increase in methadone plasma exposure (Table 3, FIG. 3).

TABLE 3

Mean and standard deviation (SD) Plasma methadone concentrations (ng/mL) determined by liquid chromatography/triple quadrupole mass spectrometry, AUC's and bioavailability relative to oral methadone alone in six dogs in each treatment group administered: 1) fluconazole 5 mg/kg PO q 12 h with methadone 1 mg/kg PO administered 24 hours after fluconazole was started; 2) fluconazole 2.5 mg/kg PO q 12 h with methadone 1 mg/kg PO administered 24 hours after fluconazole was started; and 3) fluconazole 5 mg/kg PO q 24 h with methadone 1 mg/kg PO administered 24 hours after fluconazole was started.

| Time (hr) | Fluconazole 5 mg/kg PO q 12 h | | Fluconazole 2.5 mg/kg PO q 12 h | | Fluconazole 5 mg/kg PO q 24 h | |
| --- | --- | --- | --- | --- | --- | --- |
| | Mean | SD | Mean | SD | Mean | SD |
| 0 | 0.0 | 0.0 | 0.0 | 0.0 | 0.0 | 0.0 |
| 0.333 | 14.0 | 31.0 | 0.8 | 0.7 | 5.8 | 7.8 |
| 0.667 | 10.3 | 11.9 | 5.2 | 4.4 | 22.4 | 42.9 |
| 1 | 24.3 | 20.3 | 16.0 | 11.3 | 33.7 | 49.4 |
| 2 | 43.6 | 26.1 | 28.4 | 17.0 | 39.9 | 38.4 |
| 4 | 42.5 | 24.5 | 23.3 | 13.7 | 31.4 | 15.2 |
| 6 | 33.9 | 19.5 | 19.2 | 10.5 | 24.0 | 13.1 |
| 8 | 27.6 | 14.8 | 15.9 | 9.4 | 18.4 | 10.5 |
| 12 | 20.2 | 7.7 | 11.6 | 8.6 | 15.3 | 8.7 |
| 24 | 8.3 | 3.0 | 5.6 | 6.8 | 5.5 | 2.4 |
| Mean dose normalized AUC (to infinity) (hr*ng/mL) | 734.3 | | 397.4 | | 515.3 | |
| Bioavailability (mean) relative to oral methadone alone | 11936% | | 6459% | | 8376% | |

Example II

In this example, incorporation of naltrexone was tested as an abuse deterrent in oral opioid formulation in dogs. Naltrexone is an example of an opioid antagonist metabolized by different pathways than methadone. The purpose of this study was to assess the effects of incorporating naltrexone at a fixed ratio to an oral formulation containing methadone and fluconazole for use in dogs which will decrease human abuse/misuse potential or the consequences of inadvertent drug exposure (e.g. an infant eating a tablet/capsule).

Methods

Twelve healthy Beagle dogs were divided into two groups of 6 each in a parallel study design. Both groups were administered a dose of fluconazole, 5 mg/kg PO 12 hours prior to methadone administration. Group 1 was administered a combination of methadone (1 mg/kg) and fluconazole (5 mg/kg) PO (FDA approved crushed tablets weighed and placed in a gelatin capsule). Group 2 was administered a combination of methadone (1 mg/kg) and fluconazole (5 mg/kg) with naltrexone (0.25 mg/kg) PO (FDA approved crushed tablets weighed and placed in a gelatin capsule). Rectal temperature was monitored as a marker of central opioid effects throughout the study. Blood was obtained at predetermined intervals for the determination of plasma methadone, naltrexone, β-naltrexol (an active metabolite), and naltrexone glucuronide (an inactive metabolite, but confirmation of naltrexone exposure).

Results

Figure 4:
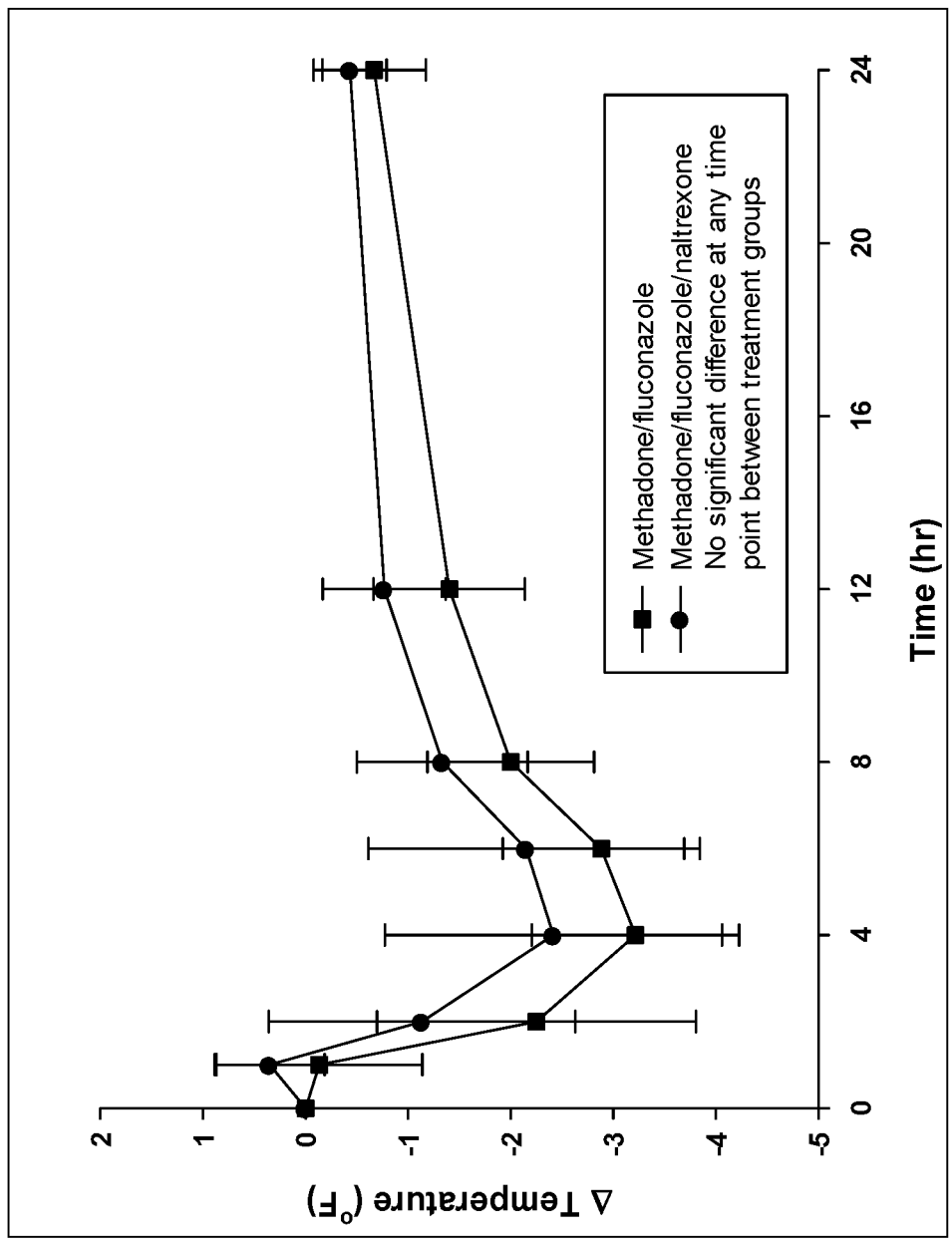
FIG. 4 is a chart showing changes in rectal temperature (from baseline) in two groups of six dogs each administered either methadone (1 mg/kg) with fluconazole (5 mg/kg) PO or methadone (1 mg/kg) with fluconazole (5 mg/kg) and naltrexone (0.25 mg/kg) PO.
Figure 5A:
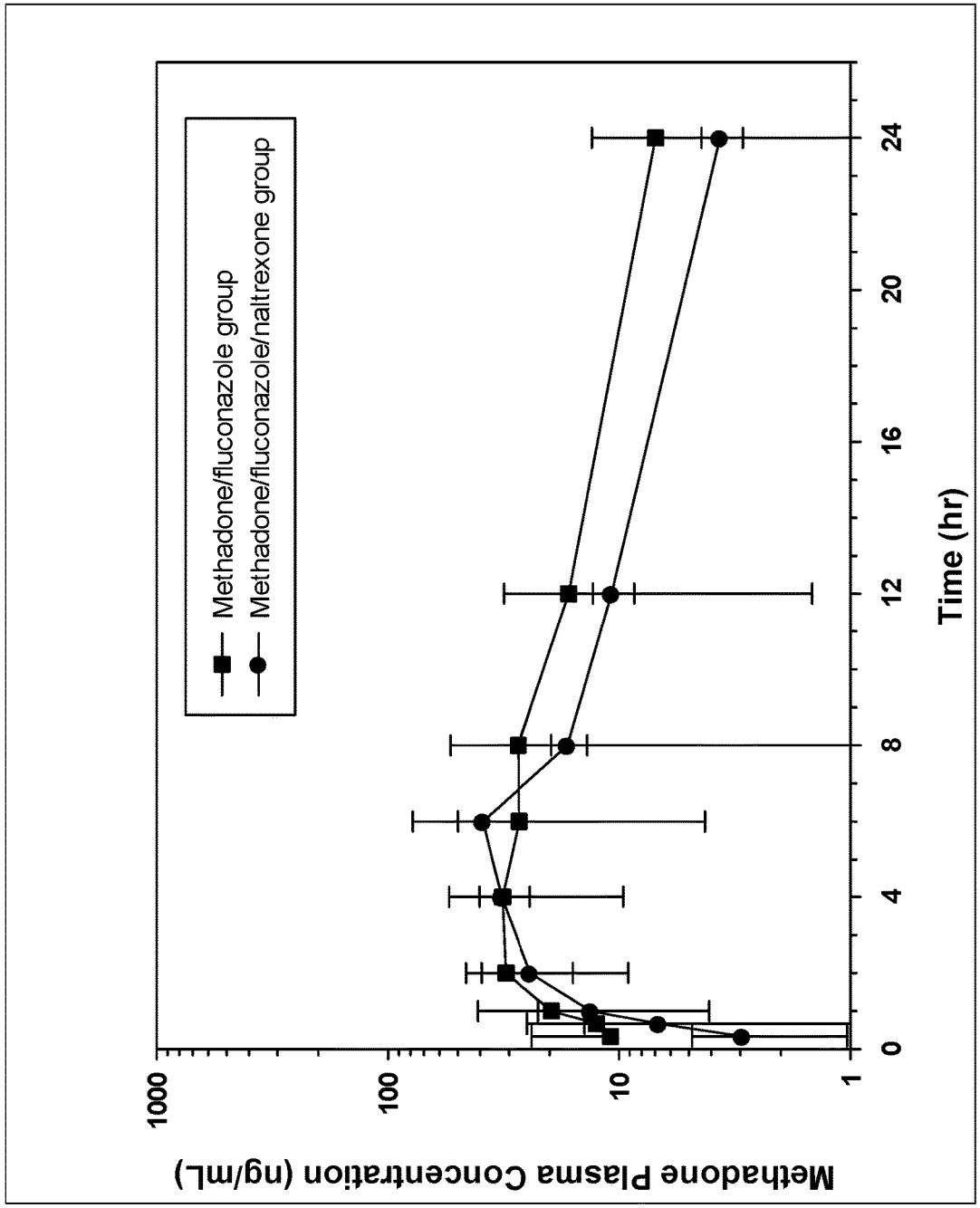
FIGS. 5A and 5B are charts showing plasma drug concentrations in two groups of six dogs each administered either methadone (1 mg/kg) with fluconazole (5 mg/kg) PO or methadone (1 mg/kg) with fluconazole (5 mg/kg) and naltrexone (0.25 mg/kg) PO, with FIG. 5A showing plasma methadone concentrations and FIG. 5B showing plasma naltrexone glucuronide (inactive metabolite) concentrations in the group administered oral naltrexone, noted that the active antagonist components naltrexone and β-naltrexol were only sporadically detected around the LOQ of 1 ng/mL.
Figure 5B:
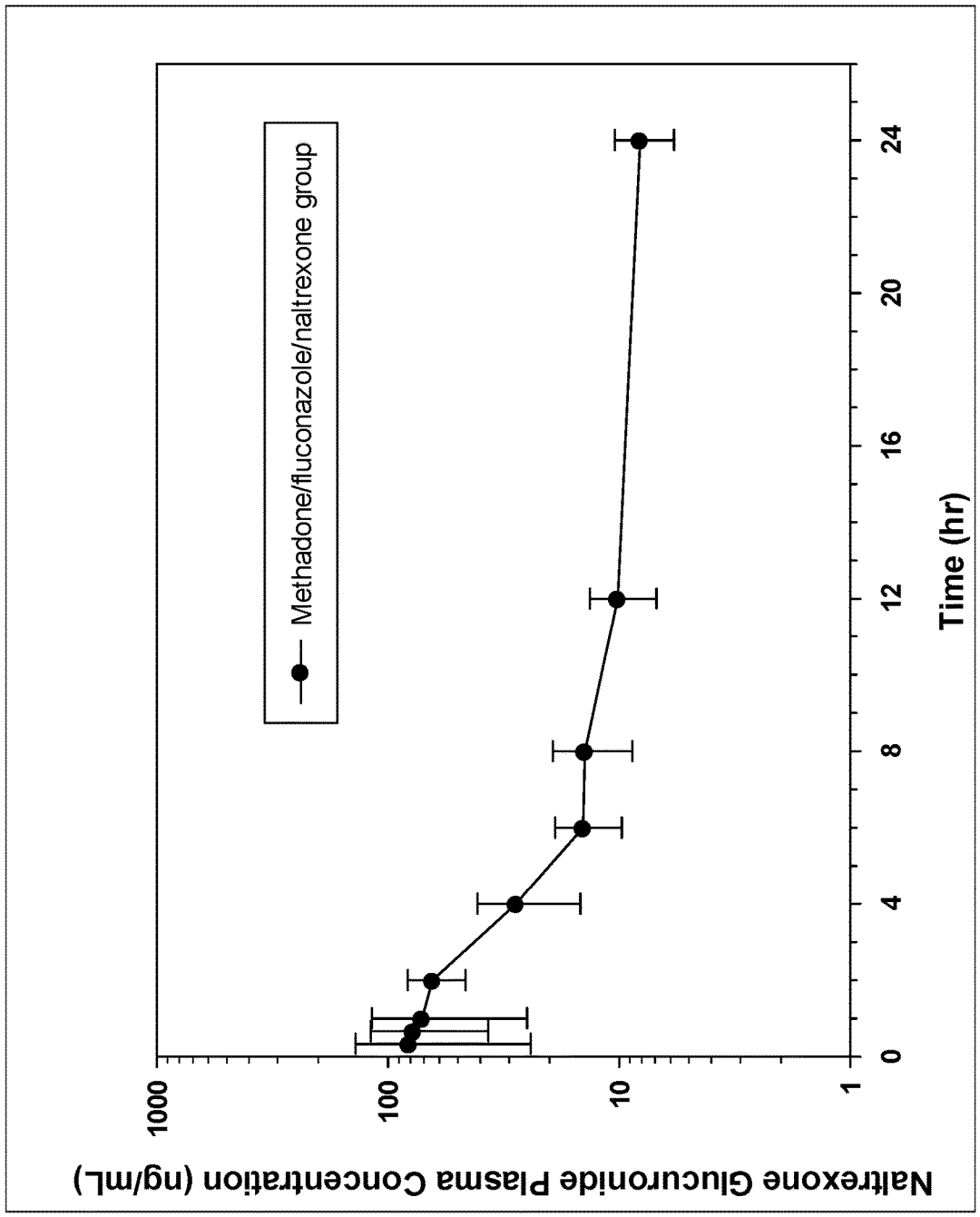

No significant differences in rectal temperature occurred between the groups (P>0.05, FIG. 4), and rectal temperature in both groups were decreased compared to baseline from 1-12 hours after administration of methadone. Similar concentrations of methadone occurred in both treatment groups, and naltrexone glucuronide was detected in the group administered naltrexone, but not in the other group (FIGS. 5A, 5B). The active antagonist components, naltrexone and β-naltrexol were rarely detected above the LOQ of the assay (1 ng/mL).

Conclusions

Addition of naltrexone to a formulation of methadone and fluconazole did not affect the central opioid effects of methadone when administered with fluconazole orally. Only the inactive metabolite of naltrexone was consistently measured in dogs administered naltrexone. Addition of naltrexone without special formulation preparation (e.g. sequestration) to an opioid formulation (methadone, fluconazole) can produce a human abuse/misuse deterrent and protect against accidental drug exposure in humans without affecting the opioid effects in dogs. This is the first time this strategy has been demonstrated in veterinary medicine.

Example III

In this example, multiple doses of a novel oral opioid formulation containing an abuse deterrent in dogs were evaluated. The purpose of this study was to assess the effects of multiple doses (4 doses) of a novel opioid formulation containing methadone, fluconazole and naltrexone in healthy Beagle dogs. The dose regimens were designed to simulate regimens that could be used in surgical patients for the control of postoperative pain.

Methods

Twelve healthy Beagle dogs were divided into two groups of 6 each in a parallel study design. Both groups were administered a novel oral opioid formulation containing methadone, fluconazole and naltrexone from FDA approved crushed tablets weighed and placed in a gelatin capsule according the dosing in Table 4. Group 1 simulated a patient dropped off the night before surgery, while Group 2 simulated a patient dropped off in the morning for same day early afternoon surgery. Rectal temperature was monitored as a marker of central opioid effects throughout the study and von Frey thresholds were obtained to assess the antinociceptive effects. Blood was obtained at predetermined intervals for the determination of plasma methadone, naltrexone, β-naltrexol (an active naltrexone metabolite) and naltrexone glucuronide (an inactive metabolite, but confirmation of naltrexone exposure).

TABLE 4

Dosing schedule for multiple dose study.

| Day | Time | Group 1 Dose (PO) | Group 1 Plasma Samples (hours after dose) |
|---|---|---|---|
| Day 1 | 6p | Methadone, 1 mg/kg: fluconazole, 5 mg/kg: naltrexone 0.25 mg/kg | 0, 1, 2, 4, 14 |
| Day 2 | 8a | Methadone, 1 mg/kg: fluconazole, 5 mg/kg: naltrexone 0.25 mg/kg | 0.5, 1, 2, 4, 6, 10 |
| Day 2 | 12p | — | — |
| Day 2 | 6p | Methadone, 0.5 mg/kg: fluconazole, 2.5 mg/kg: naltrexone 0.125 mg/kg | 1, 2, 4, 14 |
| Day 3 | 8a | Methadone, 0.5 mg/kg: fluconazole, 2.5 mg/kg: naltrexone 0.125 mg/kg | 0.5, 1, 2, 4, 8, 12, 24, 32 |

| Day | Time | Group 2 Dose (PO) | Group 2 Plasma Samples (hours after dose) |
|---|---|---|---|
| Day 1 | 6p | — | — |
| Day 2 | 8a | Methadone, 1 mg/kg: fluconazole, 5 mg/kg: naltrexone 0.25 mg/kg | 0, 2, 4 |
| Day 2 | 12p | Methadone, 0.5 mg/kg: fluconazole, 2.5 mg/kg: naltrexone 0.125 mg/kg | 1, 2, 4 |
| Day 2 | 6p | Methadone, 0.5 mg/kg: fluconazole, 2.5 mg/kg: naltrexone 0.125 mg/kg | 0.5, 1, 2, 4, 14 |
| Day 3 | 8a | Methadone, 0.5 mg/kg: fluconazole, 2.5 mg/kg: naltrexone 0.125 mg/kg | 0.5, 1, 2, 4, 8, 12, 24, 32 |

Results

Figure 6A:
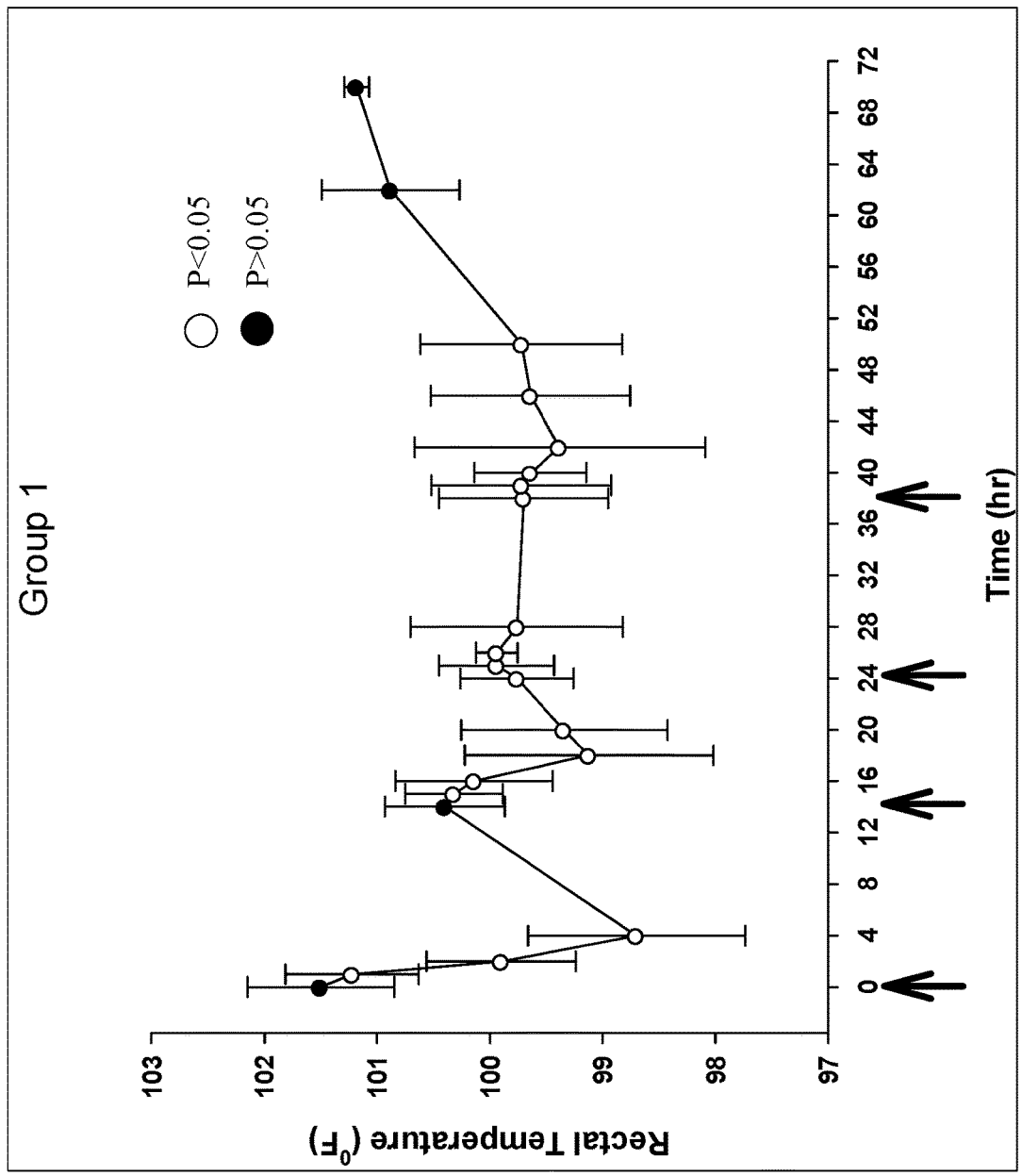
FIGS. 6A and 6B are charts showing rectal temperature of Group 1 (FIG. 6A) and Group 2 (FIG. 6B) after oral administration of multiple doses of a formulation containing a fixed ratio of methadone, fluconazole and naltrexone, wherein rectal temperatures were significantly decreased (P<0.05) after all doses (including the first dose) of the formulation, and the arrows indicate when the oral doses were administered.
Figure 6B:
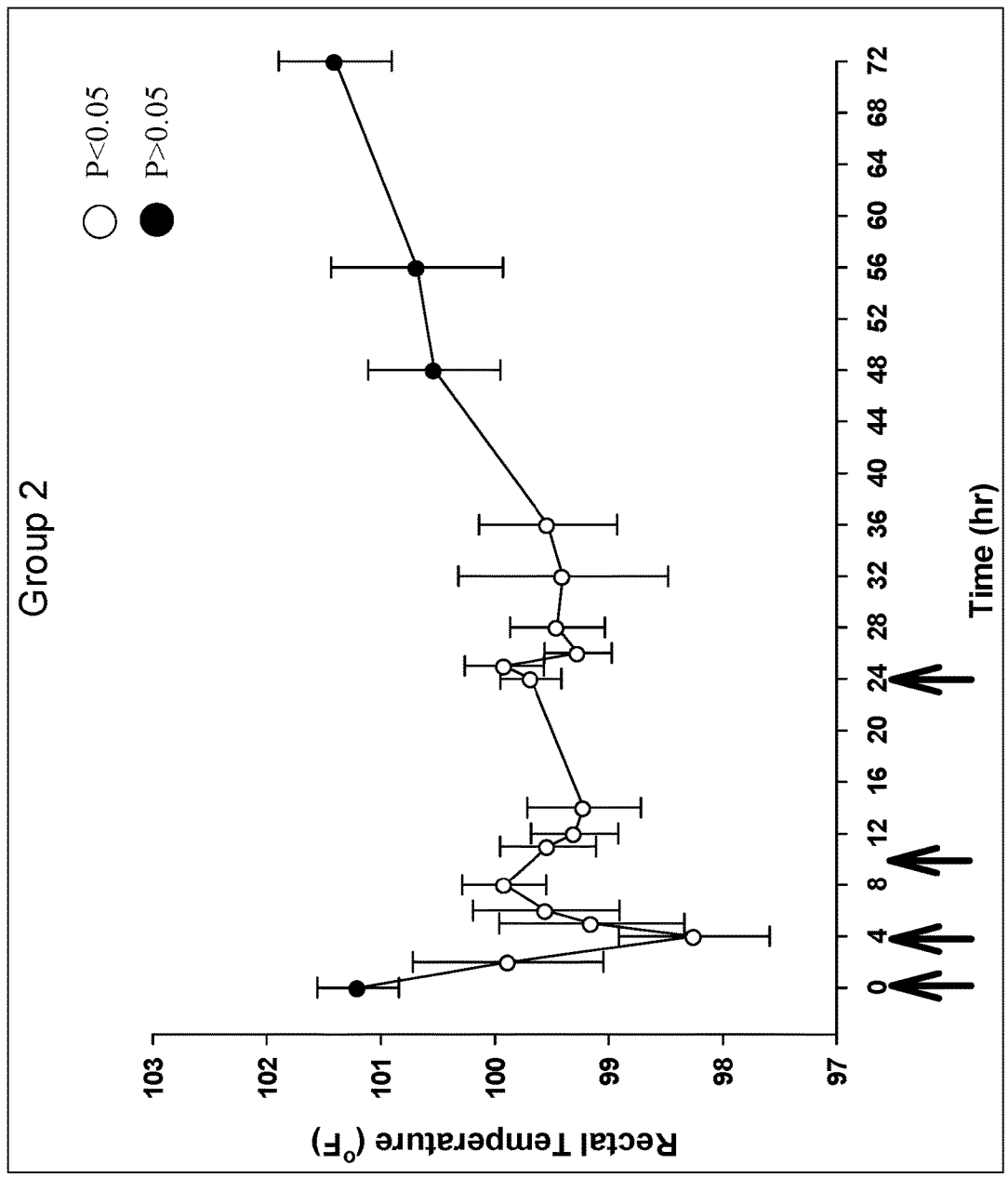
Figure 7A:
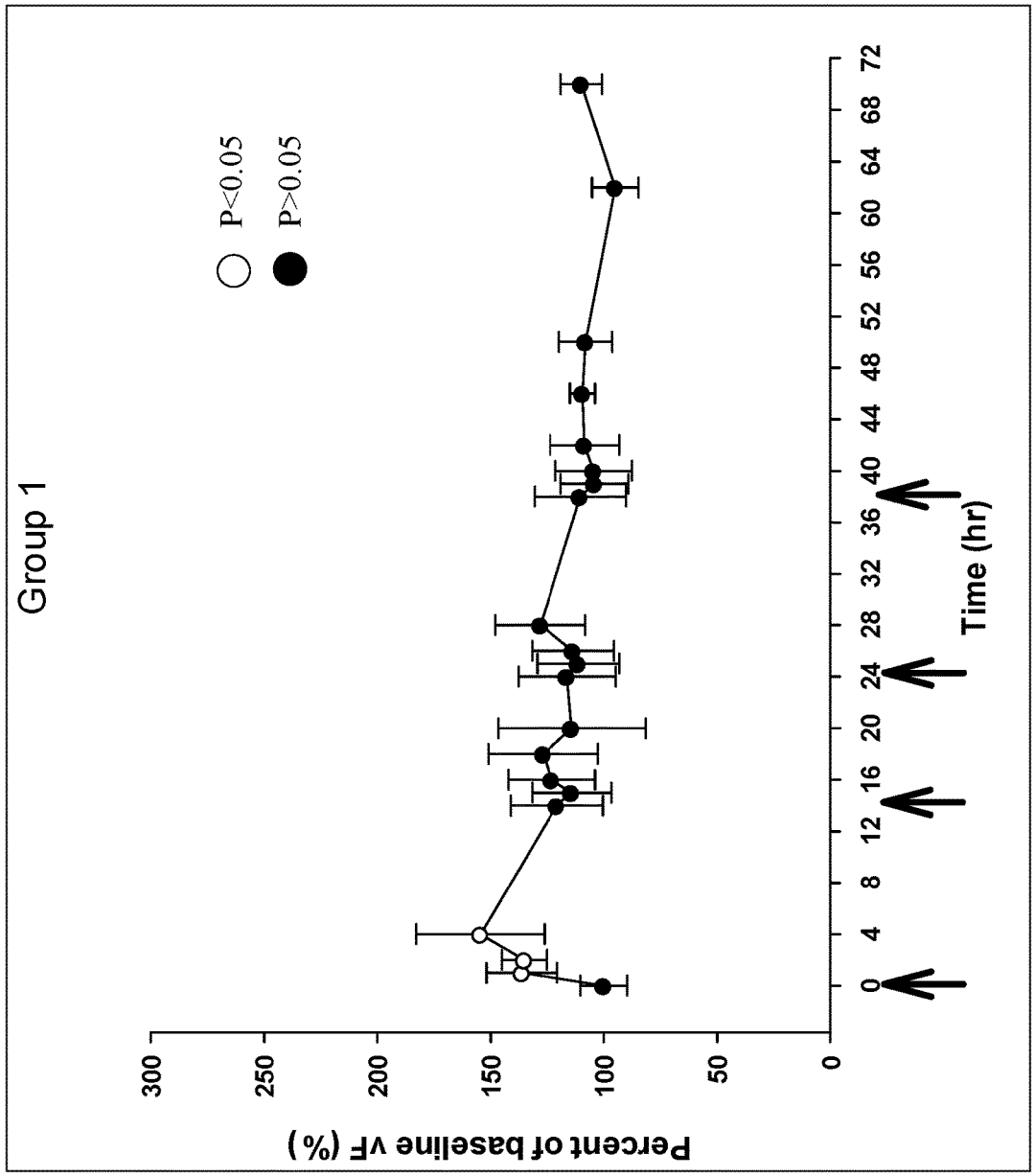
FIGS. 7A and 7B are charts showing Von Frey thresholds (percent change from baseline) of Group 1 (FIG. 7A) and Group 2 (FIG. 7B) after oral administration of multiple doses of a formulation containing a fixed ratio of methadone, fluconazole and naltrexone, wherein von Frey thresholds were significantly increased (P<0.05) at specified time points after oral dosing (including the first dose) of the formulation, and the arrows indicate when the oral doses were administered.
Figure 7B:
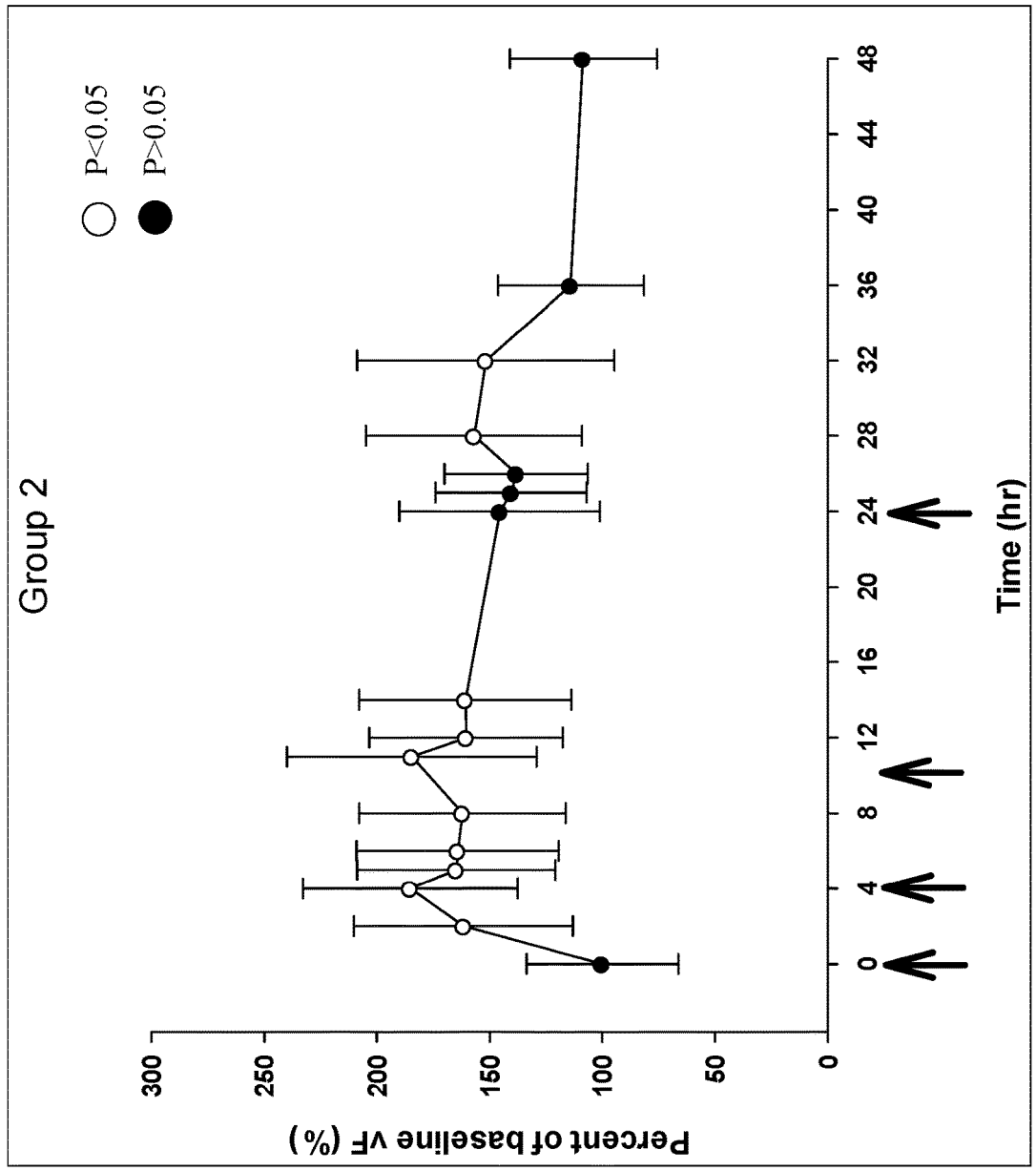
Figure 8A:
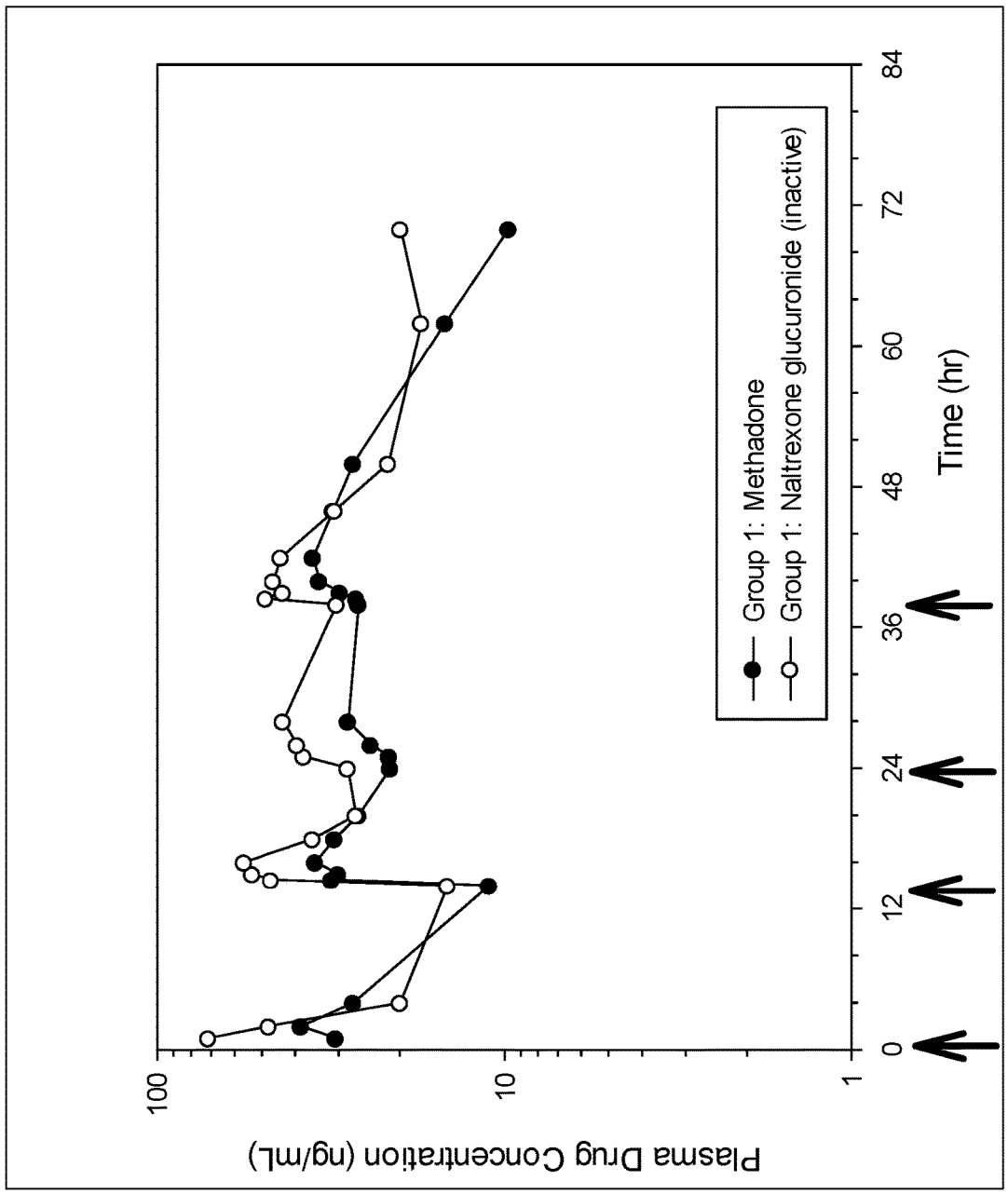
FIGS. 8A and 8B are charts showing mean plasma profiles of methadone and naltrexone glucuronide (an inactive metabolite) in Group 1 (FIG. 8A) and Group 2 (FIG. 8B) after oral administration of multiple doses of a formulation containing a fixed ratio of methadone, fluconazole and naltrexone, wherein the arrows indicate when the oral doses were administered.
Figure 8B:
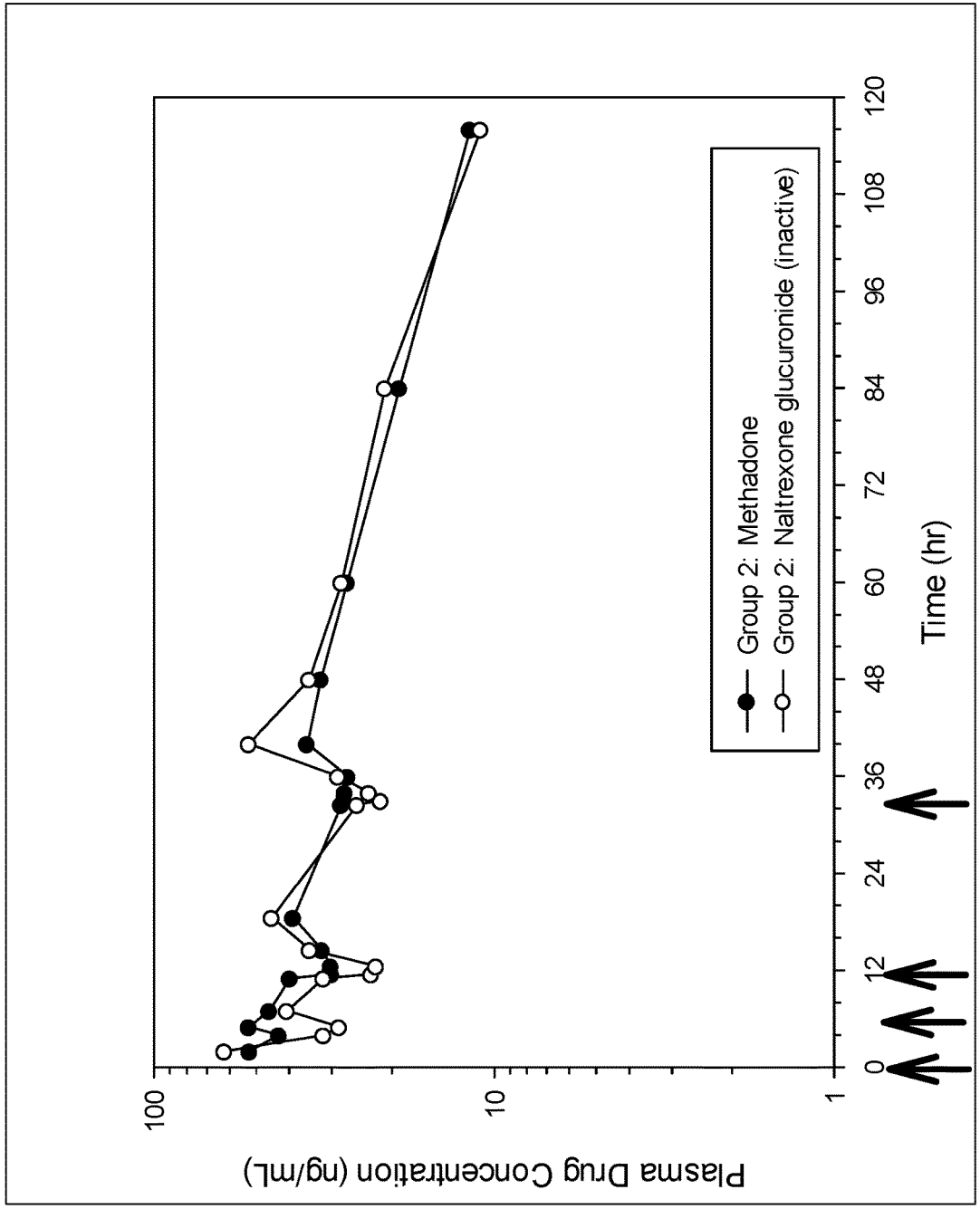

Rectal temperature was significantly decreased from baseline in both groups (P<0.05, FIGS. 6A, 6B) throughout the dosing interval and for 12 hours after the last dose (except 1 time point in Group 1, 12 hours after the first dose). Rectal temperature was even significantly decreased after the first dose in both groups indicating opioid effects without pretreating with fluconazole. Baseline and subsequent von Frey measurements were quite variable (FIG. 7A, 7B), note standard deviations. However, significant antinociceptive effects occurred in both groups, including after the first dose. Mean plasma concentrations of methadone exceeded 10 ng/mL in both treatment groups throughout the dosing and for at least 12 hours after the last dose (including after the first dose, FIG. 8A, 8B). Naltrexone glucuronide was detected in both groups, indicating naltrexone exposure, but the active antagonist components, naltrexone and β-naltrexol were rarely detected above the LOQ of the assay (1 ng/mL). The dogs tolerated the treatment well with sedation observed as an adverse effect.

Conclusions

Significant central mediated opioid effects and antinociception (analgesia) were measured after multiple doses of the opioid formulation containing an abuse deterrent. Plasma concentrations of methadone were consistent throughout the dosing intervals and for at least 12 hours after the last dose. Only the inactive metabolite of naltrexone was consistently measured in dogs. These data indicate multiple doses of an oral opioid formulation containing an opioid antagonist provide significant opioid effects within 1-2 hours of the first dose (no need for a loading dose of fluconazole), can maintain consistent effects throughout multiple doses, are interchangeable and were well tolerated.

Example IV

In this example, an opioid formulation containing a human abuse/misuse deterrent was evaluated in a clinical trial of dogs undergoing ovariohysterectomy (OHE) surgery. The purpose of this study was to assess the effects of a novel opioid formulation containing methadone, fluconazole, and the abuse deterrent naltrexone in healthy dogs undergoing OHE. The specific objective of the study was to assess a dose range of the oral opioid formulation (0.5 and 1 mg/kg methadone dose) containing fluconazole and an abuse deterrent administered every 12 hours and compare with an established effective drug approved for use in dogs, methadone injection 0.5 mg/kg SC q 4 h. The pivotal measure for treatment success was defined as adequate analgesia so that a rescue analgesic dose did not need to be administered. A secondary success was defined as no significant difference in GCPS between groups at any time point. Adverse effects were recorded.

Methods

A target of 45 otherwise healthy dogs was to be enrolled into the study and randomly divided into 3 groups of 15 in a blinded study (the evaluators did not know the treatments). Group 1 (injection) received methadone starting at 7:30 a on the day of surgery (Table 5) and then administered every 4 hours for 4 total doses (last dose at 8 p). Group 2 (0.5 mg/kg PO) received an oral opioid formulation 14 hours prior to surgery (6 p the day before the surgery) at a loading dose of 1 mg/kg:5 mg/kg:0.25 mg/kg of methadone:fluconazole:naltrexone, followed by 0.5 mg/kg:2.5 mg/kg:0.125 mg/kg of methadone:fluconazole:naltrexone at 7:30 a the morning of the surgery and 8 p the day of the surgery for a total of 3 doses (approximately q 12 h). Group 3 (1 mg/kg PO) received an oral opioid formulation 14 hours prior to surgery (6 p the day before the surgery) at a dose of 1 mg/kg:5 mg/kg:0.25 mg/kg of methadone:fluconazole:naltrexone, followed by the same dose at 7:30 a the morning of the surgery and 8 p the day of the surgery for a total of 3 doses (approximately q 12 h). All animals received acepromazine (0.05 mg/kg SC) as a premedication at least 30 minutes prior to IV catheter placement (7:30 a the morning of surgery). Anesthesia was induced with IV propofol at a dose titrated to allow intubation and anesthesia was maintained using isoflurane in oxygen. Anesthesia was monitored by licensed veterinary technicians. All animals received IV lactated ringer's solution during surgery (5 ml/kg/hr). Surgery was done in a standardized manner by experienced surgeons. Blood was obtained by venipuncture at 4:00 p and 8:00 p the day of surgery (Day 1) and at 5:00 p the day after surgery (approximately 21 hours after the last methadone dose) for determination of methadone, fluconazole, naltrexone and naltrexone metabolite concentrations.

TABLE 5

Schedule of treatments and assessments in 43 dogs undergoing ovariohysterectomy (OHE). Oral lactose tablets were administered to the 0.5 mg/kg methadone injection group and saline injections (equivalent volume to methadone injections) were administered to the oral methadone groups.

| Study Day | Time | Animal Measurements | Oral Drug/ Placebo Administration | Methadone/ Placebo injection | Other treatments | Procedures |
|---|---|---|---|---|---|---|
| Day 0 | 6:00 P | GCPS, Sedation, rectal temperature | Methadone PO Dose 1 | | | |
| Day 1 | 7:30 A | | Methadone PO dose 2 | Injection 1 | Acepromazine, premed/sedation | |
| | 8:00 A | | | | Propofol induction, Isoflurane maintenance | Catheter Placement, Anesthesia Induction starts, surgeries start |
| | 12:00 p | GCPS, Sedation, rectal temperature | | Injection 2 | | Surgeries complete |
| | 1:00 P | GCPS, Sedation, rectal temperature | | | | |
| | 4:00 P | GCPS, Sedation, rectal temperature | | Injection 3 | | Blood Draw |
| | 6:00 P | GCPS, Sedation, rectal temperature | | | | |
| | 8:00 P | GCPS, Sedation, rectal temperature | Methadone PO Dose 3 | Injection 4 | | Blood draw |
| Day 2 | 6:30 A | GCPS, Sedation, rectal temperature | Carprofen PO Dose 1 | | | |
| | 5:00 P | GCPS, Sedation, rectal temperature | | | | Blood draw |
| Day 3 | 7:00 A | GCPS, Sedation, rectal temperature | Carprofen PO Dose 2 | | | |

Preanesthetic sedation and ease of catheter placement was assessed in each dog (Table 6). A validated pain scale (Glasgow Composite Pain Scale—GCPS) was used to assess a baseline prior to surgery and postoperative pain. A treatment failure occurred when a rescue analgesic was administered (morphine 0.25 mg/kg SC) if the GCPS exceeded a total score of 6, when the animal was mobile or total score of 5 when the animal was immobile. All dogs were administered oral carprofen approximately 24 hours after surgery, which was 12 hours after the last opioid dose.

TABLE 6

Pre-anesthetic evaluation of sedation, ease of IV catheter placement and time from premedication administration to IV catheter placement in 43 dogs undergoing ovariohysterectomy surgery. All patients were also administered acepromazine, 0.05 mg/kg SC. There were no significant differences in the time after premedication administration to IV catheter placement (P = 0.934). The three treatment groups were injectable methadone administered at 0.5 mg/kg SC q 4 hours, or a novel opioid formulation containing an abuse deterrent at either 0.5 or 1 mg/kg (methadone) PO every 12 hours.

| | Methadone Treatment | | |
|---|---|---|---|
| Pre-anesthetic Evaluations | 0.5 mg/kg SC q 4 h | 0.5 mg/kg PO q 12 h | 1 mg/kg PO q 12 h |
| Pre-anesthetic sedation | | | |
| A. None - no apparent effect | 0 | 1 | 0 |
| B. Mild - drowsy, but still active | 7 | 14 | 13 |
| C. Moderate - drowsy, glazed eyes, but still able to walk without assistance | 3 | 0 | 1 |
| D. Heavy - Very drowsy, unable to walk or requires assistance to walk | 3 | 0 | 1 |
| IV Catheter placement | | | |
| A. Unable to restrain the dog | 0 | 0 | 0 |
| B. The dog was restrained, but was difficult | 2 | 5 | 3 |
| C. The dog was restrained with little effort | 8 | 10 | 12 |
| D. The dog was unable to sit sternal and had to be supported | 3 | 0 | 0 |

TABLE 6-continued

Pre-anesthetic evaluation of sedation, ease of IV catheter placement and time from premedication administration to IV catheter placement in 43 dogs undergoing ovariohysterectomy surgery. All patients were also administered acepromazine, 0.05 mg/kg SC. There were no significant differences in the time after premedication administration to IV catheter placement (P = 0.934). The three treatment groups were injectable methadone administered at 0.5 mg/kg SC q 4 hours, or a novel opioid formulation containing an abuse deterrent at either 0.5 or 1 mg/kg (methadone) PO every 12 hours.

| | Methadone Treatment | | |
|---|---|---|---|
| Pre-anesthetic Evaluations | 0.5 mg/kg SC q 4 h | 0.5 mg/kg PO q 12 h | 1 mg/kg PO q 12 h |
| Mean (range) time after premedication administration to catheter placement in minutes | 101 (33-176) | 97 (32-195) | 102 (29-217) |

Results

A total of 43 dogs were enrolled in the study: 13 in the injection group, 15 in the 0.5 mg/kg PO group and 15 in the 1 mg/kg PO group. Forty-two dogs were from animal shelters or foster homes, and 1 dog was privately owned but recently adopted (adopted <1 month prior to the study). All dogs completed the study. Forty-two dogs were mixed breed dogs, and 1 was a Boxer dog. The median weight was 18.7 kg with a range of 2.7-28.0 kg. Preanesthetic sedation was satisfactory in all dogs, and IV catheters were able to be placed in all dogs (Table 6). There was no significant difference in length of time from administration of premedication to IV catheter placement (P=0.934, Kruskal-Wallis One Way Analysis of Variance on Ranks; Table 6). There was no difference in the induction doses of propofol (P=0.679, Kruskal-Wallis One Way Analysis of Variance on Ranks; Table 7).

TABLE 7

The doses of propofol administered for induction of anesthesia were not significantly different between the treatment groups (P = 0.679) using the Kruskal-Wallis one-way analysis of variance on ranks. The three treatment groups were injectable methadone administered at 0.5 mg/kg SC q 4 hours, or a novel opioid formulation containing an abuse deterrent at either 0.5 or 1 mg/kg (methadone) PO every 12 hours.

| | Propofol Induction Dose (mg/kg) | | |
|---|---|---|---|
| Methadone Treatment | Mean | Minimum | Maximum |
| 0.5 mg/kg SC q 4 h | 4.3 | 2.4 | 8.4 |
| 0.5 mg/kg PO q 12 h | 3.9 | 2.7 | 5.5 |
| 1 mg/kg PO q 12 h | 3.7 | 2.5 | 5.9 |

Figure 9:
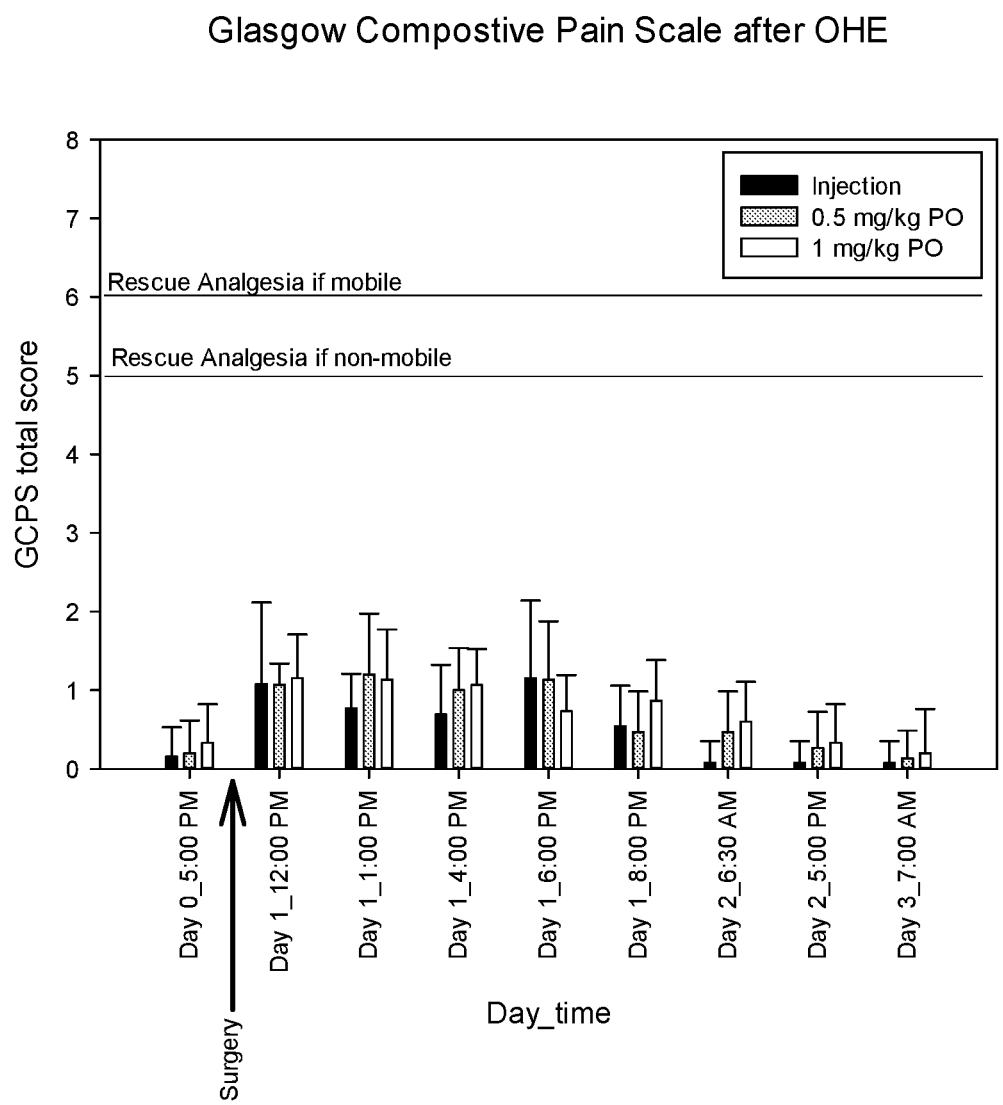
FIG. 9 is a chart showing the total score from Glasgow Composite Pain Scale (GCPS) in dogs undergoing ovariohysterectomy (OHE), and showing no significant difference between the treatment groups (P>0.05) at any time point, wherein the three treatment groups were injectable methadone administered at 0.5 mg/kg SC q 4 hours, or an oral formulation containing methadone/fluconazole/naltrexone at two dosages (0.5/2.5/0.125 mg/kg or 1/5/0.25 mg/kg) every 12 hours.

No dog failed a treatment, as none of them were administered a rescue analgesic (Table 8). The GCPS were low in all treatment groups (FIG. 9), and there were no differences between the groups at any time point (P>0.05; Kruskal-Wallis One Way Analysis of Variance on Ranks).

TABLE 8

The pivotal outcome of the study was treatment failure and the need to administer the rescue analgesic. A treatment failure was defined as a Glasgow Composite Pain Scale total score of 5 in an animal that was non-mobile (unable to walk) or 6 in a mobile animal (able to walk). No doses of rescue analgesic were administered. The three treatment groups were injectable methadone administered at 0.5 mg/kg SC q 4 hours, or a novel opioid formulation containing an abuse deterrent at either 0.5 or 1 mg/kg (methadone) PO every 12 hours.

| Treatment Outcome | 0.5 mg/kg SC q 4 h | 0.5 mg/kg PO q 12 h | 1 mg/kg PO q 12 h |
|---|---|---|---|
| Success | 13 | 15 | 15 |
| Failure | 0 | 0 | 0 |
| Total | 13 | 15 | 15 |

The most common adverse effect was perioperative nausea or vomiting in dogs, which was not significantly different between the injection group (2/13), the 0.5 mg/kg group (2/15, P=1.000), and the 1 mg/kg PO group (7/15, P=0.114) when using a Fisher exact test. Two of the dogs in the 1 mg/kg PO were administered ondansetron for vomiting >3 times. Postoperative sedation was noted for up to 12 hours (Table 9) but was only profound in the immediate postoperative period (through 4 hours in the postoperative period). Sedation was not present in any of the dogs at 24 hours postoperative assessment (12 hours after most recent methadone dose)

TABLE 9

Sedation scores at each time point in each treatment group. The three treatment groups were injectable methadone administered at 0.5 mg/kg SC q 4 hours, or a novel opioid formulation containing an abuse deterrent at either 0.5 or 1 mg/kg (methadone) PO every 12 hours. No animal was scored as unresponsive at any time.

| Treatment | Sedation Score | Day 0 5:00 PM | Day 1 12:00 PM | Day 1 1:00 PM | Day 1 4:00 PM | Day 1 6:00 PM | Day 1 8:00 PM | Day 2 6:30 AM | Day 2 5:00 PM | Day 3 7:00 AM |
|---|---|---|---|---|---|---|---|---|---|---|
| 0.5 mg/kg SC q 4 h | None | 13 | 2 | 1 | 5 | 4 | 9 | 13 | 13 | 13 |
| | Slight | 0 | 10 | 6 | 8 | 8 | 6 | 0 | 0 | 0 |
| | Moderate | 0 | 1 | 3 | 0 | 1 | 0 | 0 | 0 | 0 |
| | Profound | 0 | 0 | 3 | 0 | 0 | 0 | 0 | 0 | 0 |
| | N | 13 | 13 | 13 | 13 | 13 | 13 | 13 | 13 | 13 |
| 0.5 mg/kg PO q 12 h | None | 15 | 0 | 0 | 2 | 1 | 4 | 15 | 15 | 15 |
| | Slight | 0 | 12 | 11 | 12 | 13 | 10 | 0 | 0 | 0 |

TABLE 9-continued

Sedation scores at each time point in each treatment group. The three treatment groups were injectable methadone administered at 0.5 mg/kg SC q 4 hours, or a novel opioid formulation containing an abuse deterrent at either 0.5 or 1 mg/kg (methadone) PO every 12 hours. No animal was scored as unresponsive at any time.

| Treatment | Sedation Score | Day 0 5:00 PM | Day 1 12:00 PM | Day 1 1:00 PM | Day 1 4:00 PM | Day 1 6:00 PM | Day 1 8:00 PM | Day 2 6:30 AM | Day 2 5:00 PM | Day 3 7:00 AM |
|---|---|---|---|---|---|---|---|---|---|---|
| | Moderate | 0 | 1 | 3 | 0 | 1 | 1 | 0 | 0 | 0 |
| | Profound | 0 | 1 | 1 | 1 | 0 | 0 | 0 | 0 | 0 |
| | N* | 15 | 14 | 15 | 15 | 15 | 15 | 15 | 15 | 15 |
| 1 mg/kg PO q 12 h | None | 15 | 0 | 0 | 1 | 3 | 4 | 15 | 15 | 15 |
| | Slight | 0 | 10 | 12 | 14 | 12 | 11 | 0 | 0 | 0 |
| | Moderate | 0 | 2 | 1 | 0 | 0 | 0 | 0 | 0 | 0 |
| | Profound | 0 | 1 | 2 | 0 | 0 | 0 | 0 | 0 | 0 |
| | N* | 15 | 13 | 15 | 15 | 15 | 15 | 15 | 15 | 15 |

*indicates not all dogs were assessed at 12p on Day 1 due to the animals still recovering from anesthesia (i.e. unable to return to their kennel).

The median methadone plasma concentrations were consistently higher in the 1 mg PO treatment group with significant differences ($P<0.05$) compared to the 0.5 mg/kg PO and injection group at 4:00 PM on Day 1 and 5:00 PM on Day 2 (Table 10). The plasma concentrations were significantly higher at 5:00 PM on Day 2 in both methadone PO groups compared to the injection group. Day 1 at 8:00 PM, the plasma methadone concentrations were significantly higher in the injection group compared to 0.5 mg/kg PO group, but not compared to the 1 mg/kg PO group. Naltrexone, naltrexone-glucuronide, β-naltrexol and fluconazole were not detected in the injection group. Naltrexone was not detected in any plasma sample from any group. Naltrexone-glucuronide was measured in most of the samples in the oral methadone groups, but β-naltrexol was rarely detected (5/30 samples, LOQ 1 ng/mL) with the highest measured concentration of 1.7 ng/mL. Fluconazole was measured in all of the samples from the oral methadone groups with concentrations ranging from 1.1-7.7 μg/mL.

TABLE 10

Plasma methadone concentrations median (range). The same superscript in a row indicated significant differences ($P < 0.05$) within the row using a Kruskal-Wallis one-way analysis of variance on ranks.

| Time | 0.5 mg/kg SC q 4 h | 0.5 mg/kg PO q 12 h | 1 mg/kg PO q 12 h |
|---|---|---|---|
| Day 1; 4:00 PM | 14.4 (5.4-32.9)[1] | 20.6 (2.6-30.3)[2] | 36.2 (3.2-67.7)[1,2] |
| Day 1; 8:00 PM | 22.4 (14.8-47.7) | 17.6 (2.0-29.8)[1] | 27.7 (2.1-54.8)[1] |
| Day 2 5:00 PM | 2.0 (0-10)[1,2] | 14.1 (3.6-41.7)[2,3] | 46.7 (1.4-98.5)[1,3] |

Conclusions

An oral opioid formulation containing an abuse deterrent was effective in providing sedation in combination with acepromazine for catheter placement and for controlling postoperative pain in dogs undergoing an OHE. All 30 dogs administered oral methadone were treatment successes. Plasma concentrations persisted significantly longer in the dogs administered the oral formulation compared to the injectable formulation group. All treatments were well tolerated.

Example V

In this example, an injectable opioid formulation containing an azole antifungal was compared to the standard opioid formulation in a preliminary safety and pharmacokinetic study. The purpose of this study was to assess the duration of plasma drug exposure and tolerability following administration of an injectable opioid formulation containing an azole antifungal and compare to the standard opioid formulation.

Methods

Five healthy mixed breed, purpose bred dogs were included in this study. Two dogs were administered two doses of the commercially available methadone solution for injection IV at times 0 and four hours, two dogs were administered the novel injectable opioid formulation containing an azole antifungal IV at times 0 and four hours and one dog was administered the injectable opioid formulation containing an azole antifungal subcutaneously (SC) at times 0 and four hours. The dose of methadone was 0.5 mg/kg in all dogs and the dogs receiving fluconazole were administered fluconazole at a dose of 2.5 mg/kg. The commercially available formulation of methadone contained 10 mg/mL in an aqueous solution while the injectable opioid formulation containing an azole antifungal subcutaneously was in solution of PEG-400 (45%), ethanol (5) and water with methadone 5 mg/mL and fluconazole 25 mg/mL. Fluconazole was initially dissolved in 90% PEG-400 with 10% ethanol, then an aqueous solution of methadone was added in equal volumes to yield the final novel injectable opioid formulation. Blood was obtained by jugular venipuncture at predetermined times (FIG. 10, 11) for the determination of methadone and fluconazole by liquid chromatography with mass spectrometry. Blood was obtained immediately prior to the 4 hour dose (i.e. a trough sample).

Results

Figure 10:
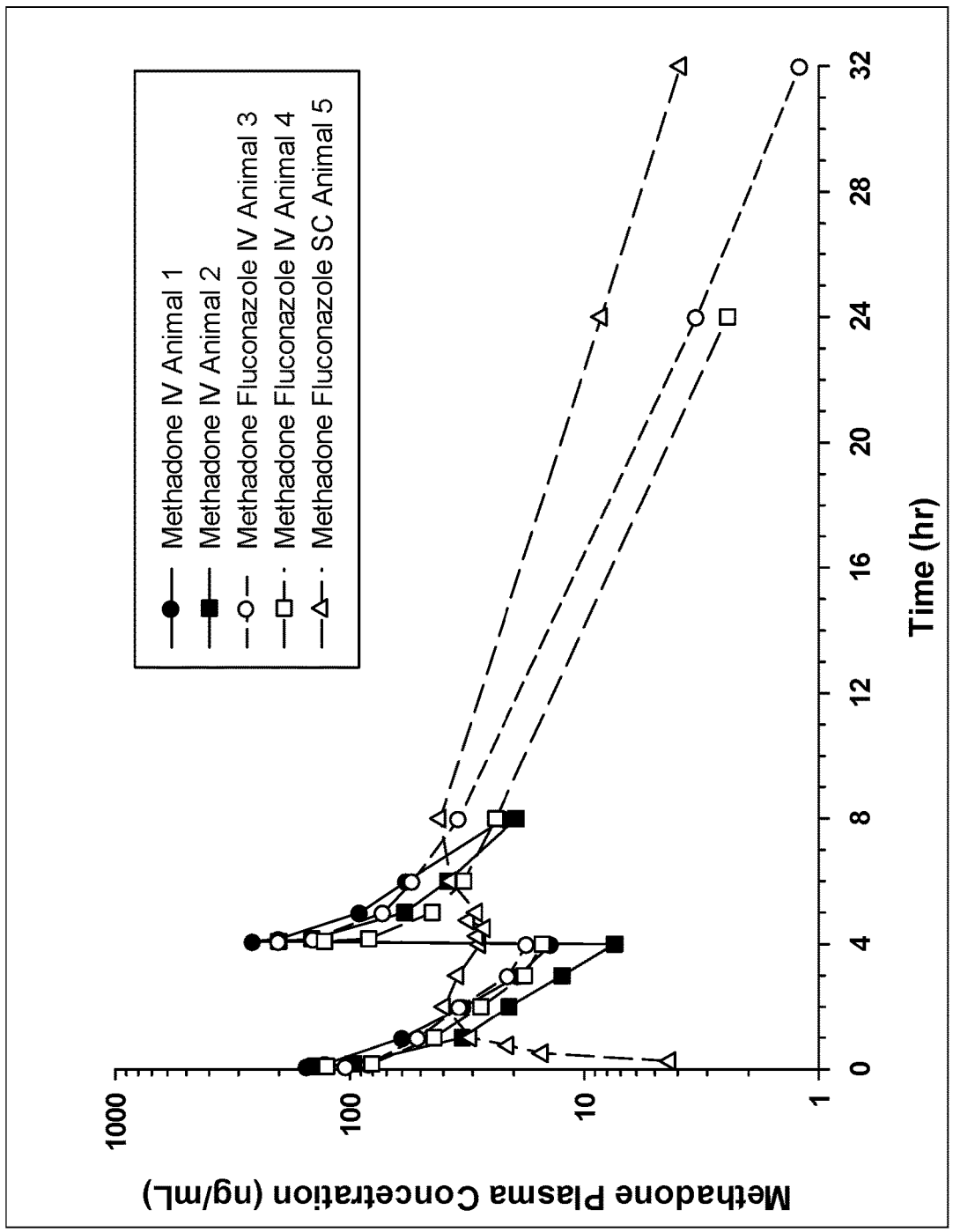
FIG. 10 is a chart showing the plasma concentrations of methadone when administered standard commercially available formulation of methadone (10 mg/mL) at time 0 and 4 hours (dogs 1 and 2) and an injectable opioid formulation (methadone 5 mg/mL) containing an azole antifungal (25 mg/mL) intravenously (dogs 3 and 4) or subcutaneously (dog 5) at times 0 and 4 hours.
Figure 11:
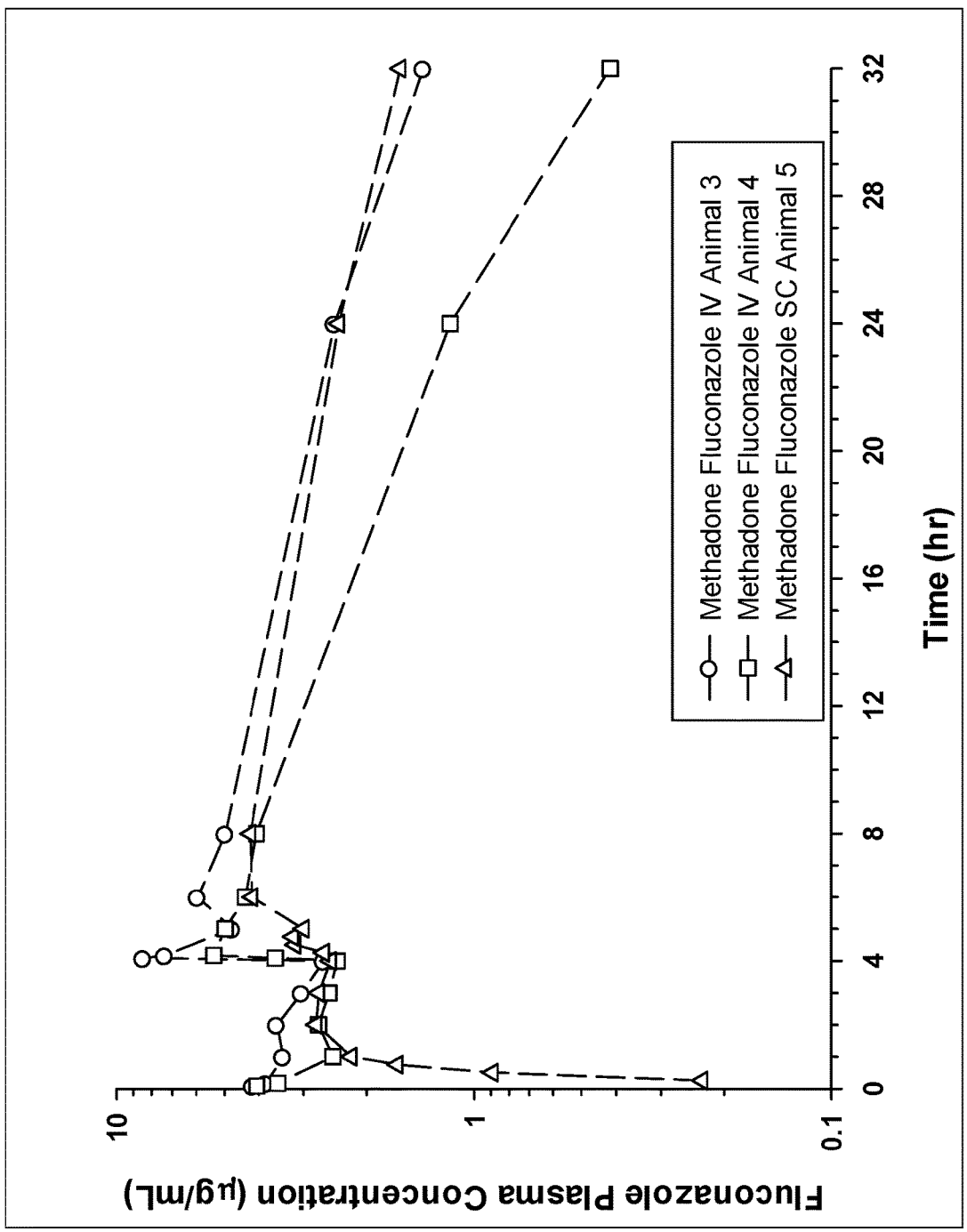
FIG. 11 is a chart showing the plasma concentrations of fluconazole when administered and injectable opioid formulation (methadone 5 mg/mL) containing an azole antifungal (25 mg/mL) intravenously and subcutaneously at times 0 and 4 hours intravenously (dogs 3 and 4) or subcutaneously (dog 5) at times 0 and 4 hours.

No serious adverse effects were noted. Sedation occurred variably in all dogs. There was no gross evidence of lesions at the injection site in any of the dogs. Methadone was only detected above 1 ng/mL at 24 hours (20 hours after the last dose) in the dogs administered the injectable opioid formulation containing an azole antifungal indicating longer drug exposure. The dog receiving the SC dose had plasma concentrations persisting the longest to at least 32 hours (28 hours after the last dose) with a concentration of 4 ng/mL (FIG. 10, 11). Fluconazole was only detected in the dogs administered the injectable opioid formulation containing an azole antifungal.

CONCLUSIONS

The methadone plasma concentrations persisted longer in the dogs administered the injectable opioid formulation containing an azole antifungal compared to the standard formulation of methadone. All IV and SC injections were well tolerated with no injection site adverse effects notes. The only adverse effect noted was sedation.

The invention claimed is:

1. A method of providing an analgesic effect in a dog comprising administering to the dog a pharmaceutical composition comprising methadone, fluconazole, and an abuse deterrent, wherein the pharmaceutical composition is administered by enteral or parenteral administration.

2. The method of claim 1, wherein the methadone and the fluconazole are administered to the dog at a weight ratio of methadone to fluconazole of about 1:1 to about 1:20.

3. The method of claim 1, wherein the methadone is administered at a dose of about 0.1 mg/kg to about 10 mg/kg.

4. The method of claim 1, wherein the fluconazole is administered at a dose of about 0.2 mg/kg to about 20 mg/kg.

5. The method of claim 1, comprising administering the composition to the dog by enteral administration.

6. The method of claim 1, comprising administering the composition to the dog as a parenteral formulation.

7. The method of claim 1, wherein the pharmaceutical composition is in a form selected from the group consisting of tablet, capsule, solution, or suspension.

8. The method of claim 7, wherein the pharmaceutical composition is in the form of a liquid suspension or solution comprising polyethylene glycol, ethanol, and/or water.

9. The method of claim 8, wherein the pharmaceutical composition comprises from about 10 mg/mL to about 50 mg/mL of fluconazole.

10. The method of claim 1, wherein the abuse deterrent comprises an opioid antagonist.

11. The method of claim 10, wherein the abuse deterrent comprises naltrexone.

12. The method of claim 1, wherein the methadone and abuse deterrent are administered to the dog at a weight ratio of methadone to abuse deterrent of about 30:1 to about 1:1.

13. The method of claim 1, wherein the abuse deterrent is administered at a dose of about 0.001 mg/kg to about 5 mg/kg.

14. The method of claim 1, wherein the methadone and the fluconazole are administered to the dog at a weight ratio of methadone to fluconazole of about 1:2.5 to about 1:10.

15. The method of claim 1, wherein the methadone is administered at a dose of about 0.5 mg/kg to about 2 mg/kg, and the fluconazole is administered at a dose of about 1 mg/kg to about 10 mg/kg.

16. A method of providing an analgesic effect in a dog comprising administering to the dog methadone and fluconazole, wherein the methadone is administered at a dose of about 0.1 mg/kg to about 10 mg/kg and/or the fluconazole is administered at a dose of about 0.2 mg/kg to about 20 mg/kg.

17. The method of claim 16, wherein the administering comprises enteral or parenteral administration.

18. The method of claim 16, wherein the methadone and the are administered to the dog at a weight ratio of methadone to fluconazole of about 1:1 to about 1:5.

19. The method of claim 16, wherein the methadone and the fluconazole are administered as a single pharmaceutical composition comprising an abuse deterrent.

20. The method of claim 16, wherein the methadone is administered at a dose of about 0.1 mg/kg to about 10 mg/kg and the fluconazole is administered at a dose of about 0.2 mg/kg to about 20 mg/kg.

21. The method of claim 16, wherein the methadone and the fluconazole are administered to the dog at a weight ratio of methadone to fluconazole of about 1:2.5 to about 1:10.

22. A method of providing an analgesic effect in a dog comprising administering to the dog methadone and fluconazole, wherein the methadone and the fluconazole are administered to the dog at a weight ratio of methadone to fluconazole of about 1:1 to about 1:5.

23. The method of claim 22, wherein the administering comprises enteral or parenteral administration.

24. The method of claim 22, wherein the methadone is administered at a dose of about 0.1 mg/kg to about 10 mg/kg.

25. The method of claim 22, wherein the fluconazole is administered at a dose of about 0.2 mg/kg to about 20 mg/kg.

26. The method of claim 22, wherein the methadone is administered at a dose of about 0.1 mg/kg to about 10 mg/kg and the fluconazole is administered at a dose of about 0.2 mg/kg to about 20 mg/kg.

27. The method of claim 22, wherein the methadone and the fluconazole are administered as a single pharmaceutical composition comprising an abuse deterrent.

28. The method of claim 22, wherein the methadone is administered at a dose of about 0.5 mg/kg to about 2 mg/kg, and the fluconazole is administered at a dose of about 1 mg/kg to about 10 mg/kg.

* * * * *